(12) United States Patent
Wong

(10) Patent No.: US 8,753,630 B2
(45) Date of Patent: Jun. 17, 2014

(54) USING EGFRVIII TO IDENTIFY AND TARGET CANCER STEM CELLS

(75) Inventor: Albert J. Wong, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 814 days.

(21) Appl. No.: 12/866,719

(22) PCT Filed: Feb. 12, 2009

(86) PCT No.: PCT/US2009/000954
§ 371 (c)(1),
(2), (4) Date: Jan. 12, 2011

(87) PCT Pub. No.: WO2009/102493
PCT Pub. Date: Aug. 20, 2009

(65) Prior Publication Data
US 2011/0123533 A1 May 26, 2011

Related U.S. Application Data

(60) Provisional application No. 61/065,589, filed on Feb. 12, 2008.

(51) Int. Cl.
*A61K 39/395* (2006.01)
*C12N 5/095* (2010.01)

(52) U.S. Cl.
USPC .................. 424/135.1; 424/136.1; 424/143.1; 424/156.1; 424/174.1

(58) Field of Classification Search
None
See application file for complete search history.

(56) References Cited

U.S. PATENT DOCUMENTS

| | | | |
|---|---|---|---|
| 6,224,868 B1 | 5/2001 | Wong et al. | |
| 7,361,336 B1 * | 4/2008 | Bergstein | 424/130.1 |
| 2005/0112705 A1 | 5/2005 | Bracco et al. | |
| 2006/0147420 A1 * | 7/2006 | Fueyo et al. | 424/93.2 |
| 2007/0003528 A1 | 1/2007 | Consigny et al. | |

OTHER PUBLICATIONS

Han et al (Neuro-Oncology, 2006, Abstract for the 11th Annual Meeting, p. 428).*
Zeppernick et al (Clinical Cancer Research, Jan. 1, 2008).*
Shen; et al., "Single Variable Domain-IgG Fusion. A Novel Recombinant Approach to Fc Domain-Containing Bispecific Antibodies", Journal of Biological Chemistry (2006), 281(16):10706-10714.

* cited by examiner

*Primary Examiner* — Karen Canella
(74) *Attorney, Agent, or Firm* — Bozicevic, Field & Francis LLP; Pamela J. Sherwood

(57) ABSTRACT

A set of markers for cancer stem cells are provided. The cells can be prospectively isolated or identified from primary tumor samples, and possess the unique properties of cancer stem cells in functional assays for tumor initiation, cancer stem cell self-renewal and differentiation. In addition, cancer stem cells can be used as a predictor for disease progression. The CSC have the phenotype of being positive for expression of CD133, and for EGFRvIII. In another embodiment of the invention, compositions are provided of a bispecific reagent that recognizes CD133 and EGFRvIII, including bispecific antibodies, which are optionally conjugated to a detectable marker, chemotherapeutic agent are radionuclide for imaging or therapy.

1 Claim, 10 Drawing Sheets

Western blot (transient expression)

Coomassie staining of purified BsAb

Western blot of purified BsAb
(anti-Myc)

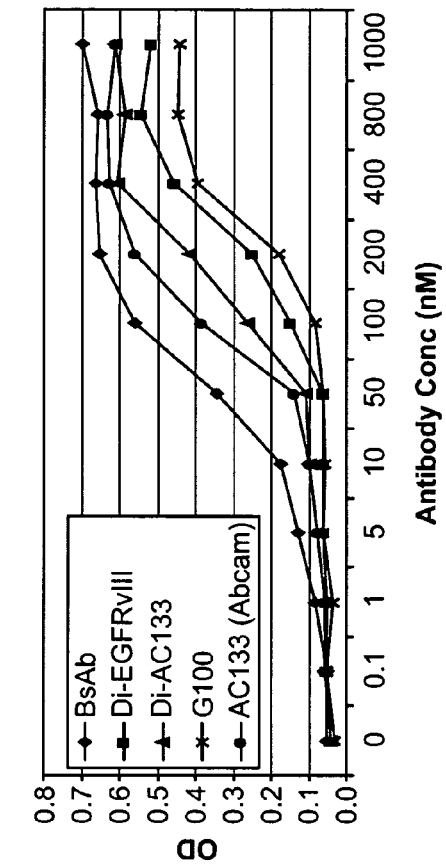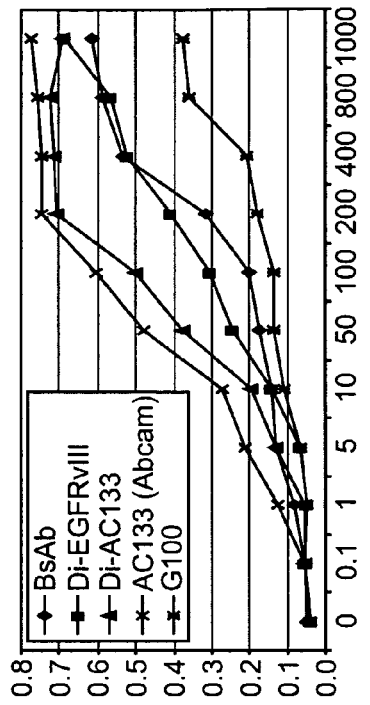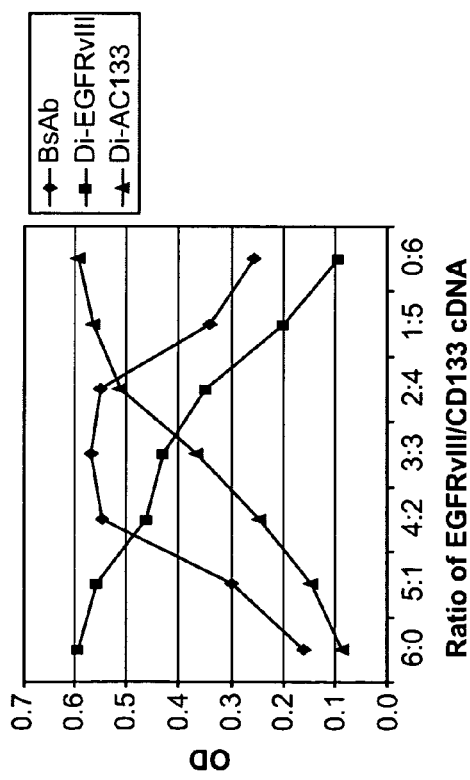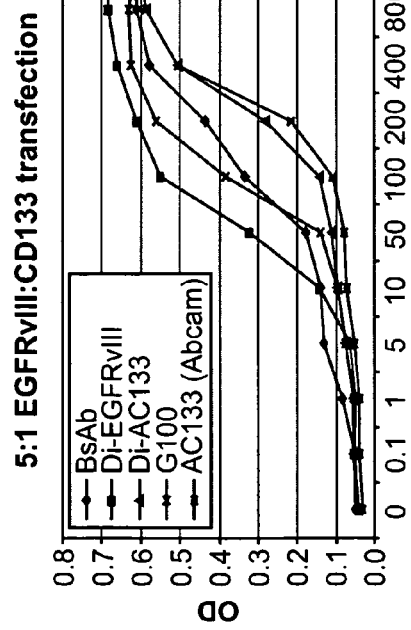
FIG. 5A
FIG. 5B
FIG. 5C
FIG. 5D

USING EGFRVIII TO IDENTIFY AND TARGET CANCER STEM CELLS

GOVERNMENT RIGHTS

This invention was made with Government support under contracts CA124832, CA 069495, and CA096539 awarded by the National Institutes of Health. The Government has certain rights in this invention.

BACKGROUND

A tumor can be viewed as an aberrant organ initiated by a tumorigenic cancer cell that acquired the capacity for indefinite proliferation through accumulated mutations. In this view of a tumor as an abnormal organ, the principles of normal stem cell biology can be applied to better understand how tumors develop and disseminate. Many observations suggest that analogies between normal stem cells and tumorigenic cells are appropriate. Both normal stem cells and tumorigenic cells have extensive proliferative potential and the ability to give rise to new (normal or abnormal) tissues. Tumorigenic cells can be thought of as cancer stem cells (CSC) that undergo an aberrant and poorly regulated process of organogenesis analogous to what normal stem cells do. Both tumors and normal tissues are composed of heterogeneous combinations of cells, with different phenotypic characteristics and different proliferative potentials.

Cancer stem cells are believed to be a small fraction of tumor cells with stem cell-like properties, which initiate and maintain neoplastic clones. These cells have the ability to self-renew, but also give rise to progenitors that yield phenotypically diverse cancer cells but with lower tumorigenic potential. This subpopulation of stem-like cells should be highly efficient at tumor formation as compared to tumor cells that are not cancer stem cells.

Cancer stem cells (CSCs) have now been identified in a wide variety of cancers including glioblastomas, medulloblastomas, colon, liver, lung, prostate, breast and ovarian tumors. While CSCs do not necessarily arise from normal stem cells, they have frequently been isolated by using markers found in normal stem cells. For example, the marker CD133 has been used to identify normal adult hematopoietic and neural stem cells. CD133 has now been successfully used to enrich for CSCs from glioblastoma, medulloblastoma, colon and prostate tumors.

The presence of cancer stem cells has profound implications for cancer therapy. At present, all of the phenotypically diverse cancer cells in a tumor are treated as though they have unlimited proliferative potential and can acquire the ability to metastasize. For many years, however, it has been recognized that small numbers of disseminated cancer cells can be detected at sites distant from primary tumors in patients that never manifest metastatic disease. One possibility is that most cancer cells lack the ability to form a new tumor such, that only the dissemination of rare cancer stem cells can lead to metastatic disease. Hence, the goal of therapy must be to identify and kill this cancer stem cell population.

Existing therapies have been developed largely against the bulk population of tumor cells, because the therapies are identified by their ability to shrink the tumor mass. However, because most cells within a cancer have limited proliferative potential, an ability to shrink a tumor mainly reflects an ability to kill these cells. Therapies that are more specifically directed against cancer stem cells may result in more durable responses and cures of metastatic tumors.

It is highly desirable to be able to identify these cancer stem cells using specific markers, and then use these markers to develop cancer stem cell specific therapeutics. In particular, despite advances in our understanding, the overall median survival for glioblastoma multiforme (GBM) remains at 11-13 months with almost 100% recurrence. The present invention addresses this issue.

SUMMARY OF THE INVENTION

A set of markers for cancer stem cells are provided. The cells can be prospectively isolated or identified from primary tumor samples, and possess the unique properties of cancer stem cells in functional assays for tumor initiation, cancer stem cell self-renewal and differentiation. In addition, cancer stem cells can be used as a predictor for disease progression. The CSC have the phenotype of being positive for expression of CD133, and for EGFRvIII.

In some embodiments of the invention, methods are provided for classification or clinical staging of cancers according to the stem cells that are present, where greater numbers of stem cells are indicative of a more aggressive cancer phenotype. Staging is useful for prognosis and treatment. In some embodiments, a tumor sample is analyzed by flow cytometry, histochemistry, including immunohistochemistry, in situ hybridization, or the like, for the presence of cells that co-express CD133 and EGFRvIII. The presence of such cells indicates the presence of CSC, and allows the definition of cancer stem cell domains in the primary tumor, as well as in metastases.

In another embodiment of the invention, compositions of isolated CSC are provided. The cells are useful for experimental evaluation, and as a source of lineage and cell specific products, including mRNA species useful in identifying genes specifically expressed in these cells, and as targets for the discovery of factors or molecules that can affect them. CSC may be used, for example, in a method of screening a compound for an effect on the cells. This involves combining the compound with the cell population of the invention, and then determining any modulatory effect resulting from the compound. This may include examination of the cells for toxicity, metabolic change, or an effect on cell function. The phenotype of CSC described herein provides a means of predicting disease progression, relapse, and development of drug resistance.

In another embodiment of the invention, compositions are provided of a bispecific reagent that recognizes CD133 and EGFRvIII, including bispecific antibodies, which are optionally conjugated to a detectable marker, chemotherapeutic agent are radionuclide for imaging or therapy.

BRIEF DESCRIPTION OF THE DRAWINGS

FIG. 5: Analysis of Dual-specificity: (A) using membrane fractions of NIH3T3 cells transfected with increasing concentration of CD133 and decreasing concentration of EGFRvIII cDNA the BsAb appears to have maximum affinity for cells expressing both epitopes. The expression of the epitopes is confirmed by the use of monospecific dimeric Di-scFv-CD133 and Di-scFv-EGFRvIII. (B-D) comparison of the relative binding affinities of monospecific antibodies with that of the BsAb in the context of epitope expression shows that the BsAb is most efficient when both epitopes are present as compared to the monospecific antibodies. In B we transfected 5 ug of cDNA for EGFRvIII and CD133, where as in ratio's of 5:1 or 1:5 we transfected either 1 ug or 5 ug respectively.

DEFINITIONS

Figure 1A:
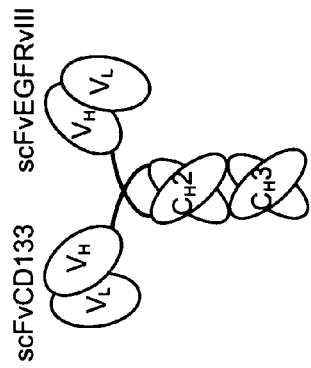
FIG. 1. construction of a bispecific antibody.

The term "stem cell" as used herein refers to a cell that (a) is capable of self-renewal; and (b) is a cell from which other types of cells can develop.

The term "progenitor cell" as used herein refers to a cell that (a) is not capable of self-renewal; and (b) is a cell from which other types of cells can develop.

The terms "cell proliferation" and "to proliferate" as used herein refer to the amplification of the cell by cell division.

The term "support" when applied to conditions under which cells are maintained, cultured, grown, proliferated, propagated or renewed, refers to conditions under which cells are capable of, respectively, being maintained, being cultured, growing, proliferating, propagating or renewing. Conditions can include cell culture media, concentrations of phosphate mimic, concentrations of stem and/or progenitor cell growth-modulating agent, or concentrations of growth factors. For example, a given cell culture media is said to "support" cell proliferation when a cell grown in said media is capable of proliferating.

As used herein, the term "isolated" when applied to a cell refers to a cell isolated from an animal, (e.g., a human, a rat, a mouse, etc.) and purified up to at least about 50%, such as 80%, 90% or more. Purity is measured by comparing the number of neural stem cells with the total number of cells. For example, an "80% pure" preparation of cancer stem cells means that 80% of the cells in the preparation are cancer stem cells.

The term "cancer stem cells" relates to cells capable of generating aggregates of undifferentiated cells, so called tumor spheres, under suitable conditions. When neural tumors are grown in culture in a defined chemical media that lacks serum but contains essential growth factors, some of the cells will begin to grow in spheres while other cells will adhere. The cells that form spheres are capable of self-renewal as when they are dissociated and grown under the same conditions, they will reform spheres. Most importantly, they represent an enrichment of CSCs as when injected into an athymic mouse host the tumor that forms recapitulates the complex histology of the original tumor and the genetic changes. It has been shown that both the spheres and the athymic mouse tumors continue to express CD133.

"EGFRvIII" is a variant of the epidermal growth factor receptor in which exons 2 through 7 are deleted. This results in an in-frame deletion of 801 bp from the cDNA and loss of 267 amino acids from the protein. Antibody that specifically recognizes EGFRvIII and not the normal EGFR can be made. PCR can also be used to assay the presence of EGFRvIII. Using PCR or antibody detection, EGFRvIII has been shown to be present in a wide variety of human tumors including those from the brain, breast, ovary, colon, lung and prostate. Expression of EGFRvIII has only been rarely noted in normal tissues.

"Bispecific antibody" and "bispecific antibodies," also known as bifunctional antibodies, refers to antibodies that recognize two different antigens by virtue of possessing at least one first antigen combining site specific for a first antigen or hapten, and at least one second antigen combining site specific for a second antigen or hapten. Such antibodies can be produced by recombinant DNA methods or include, but are not limited to, antibodies produced chemically by methods known in the art. Bispecific antibodies include all antibodies or conjugates of antibodies, or polymeric forms of antibodies which are capable of recognizing two different antigens. Bispecific antibodies include antibodies that have been reduced and reformed so as to retain their bivalent characteristics and to antibodies that have been chemically coupled so that they can have several antigen recognition sites for each antigen.

CD133 (prominin) is a 5-transmembrane domain glycoprotein. The gene encodes an 865-amino acid glycoprotein and is conserved throughout the animal kingdom. The isoform ACC133-2 lacks the 27-bp exon 3, while the longer isoform is termed AC133-1. Both isoforms encode glycosylated membrane proteins. Most of the PROML1 gene is contained in 23 exons distributed over more than 50 kb of genomic sequence. The genetic sequence of human prominin may be accessed at Genbank, accession number NM_006017.

The subject methods are useful for both prophylactic and therapeutic purposes. Thus, as used herein, the term "treating" is used to refer to both prevention of disease, and treatment of a pre-existing condition. The treatment of ongoing disease, to stabilize or improve the clinical symptoms of the patient, is a particularly important benefit provided by the present invention. Such treatment is desirably performed prior to loss of function in the affected tissues; consequently, the prophylactic therapeutic benefits provided by the invention are also important. For example, treatment of a cancer patient may be reduction of tumor size, elimination of malignant cells, prevention of metastasis, or the prevention of relapse in a patient who has been put into remission.

The terms "cell," and "cells," and "cell population," used interchangeably, intend one or more mammalian cells. The term includes progeny of a cell or cell population. Those skilled in the art will recognize that "cells" include progeny of a single cell, and the progeny can not necessarily be completely identical (in morphology or of total DNA complement) to the original parent cell due to natural, accidental, or deliberate mutation and/or change.

The term "substantially enriched" or "substantially isolated" as used herein, indicates that a cell population is at least about 20-fold, more preferably at least about 500-fold, and even more preferably at least about 5000-fold or more enriched from an original mixed cell population comprising the desired cell population.

A "subject" is a vertebrate, preferably a mammal, more preferably a human. Mammals include, but are not limited to, humans, farm animals, sport animals, and pets.

An "effective amount" is an amount sufficient to effect beneficial or desired clinical results. An effective amount can be administered in one or more administrations. For purposes of this invention, an effective amount of multivalent polypeptide is an amount that is sufficient to diagnose, palliate, ameliorate, stabilize, reverse, slow or delay the progression of the disease state.

DETAILED DESCRIPTION OF THE EMBODIMENTS

Before the present composition, methods, and isolation methodologies are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

Cancers are staged by analysis of the presence of cancer stem cells. Staging is useful for prognosis and treatment. In one embodiment of the invention, a sample from a patient is stained with reagents specific for CD133 and EGFRvIII. The analysis of staining patterns provides the relative distribution of CSC, which predicts the tumorigenicity of the tumor. In some embodiments, the sample is analyzed by flow cytometry or histochemistry for the presence of cells that co-express CD133 and EGFRvIII. In one embodiment, the patient sample is compared to a control, or a standard test value. In another embodiment, the patient sample is compared to a pre-cancer sample, or to one or more time points through the course of the disease.

Samples, including tissue sections, slides, etc. containing cancer tissue, are stained with reagents specific for markers that indicate the presence of cancer stem cells. Samples may be frozen, embedded, present in a tissue microarray, and the like. The reagents, e.g. antibodies, polynucleotide probes, etc. may be detectably labeled, or may be indirectly labeled in the staining procedure. The data provided herein demonstrate that the number and distribution of progenitor cells is diagnostic of the stage of the carcinoma.

The information thus derived is useful in prognosis and diagnosis, including susceptibility to acceleration of disease, status of a diseased state and response to changes in the environment, such as the passage of time, treatment with drugs or other modalities. The cells can also be classified as to their ability to respond to therapeutic agents and treatments, isolated for research purposes, screened for gene expression, and the like. The clinical samples can be further characterized by genetic analysis, proteomics, cell surface staining, or other means, in order to determine the presence of markers that are useful in classification. For example, genetic abnormalities can be causative of disease susceptibility or drug responsiveness, or can be linked to such phenotypes.

In another embodiment, an isolated multivalent reagent that specifically binds to CD133 and EGFRvIII surface markers is disclosed. In one aspect, the antibody is a bispecific antibody. In another aspect, the multivalent polypeptide is conjugated to a cytotoxic agent.

In another embodiment, a method for the treatment of cancer in a subject is disclosed, including administering to the subject, in an amount effective for the treatment, a pharmaceutical composition including (a) at least one multivalent reagent that (i) immunospecifically binds CD133 and EGFRvIII surface markers and (ii) exerts a cytostatic or cytotoxic effect on a subpopulation of neural cancer stem cells; and (b) a pharmaceutically acceptable carrier.

Therapeutic Agents

Generally, reagents suitable for practicing the methods of the present invention immunospecifically bind CD133 and EGFRvIII. Antibodies suitable for practicing the methods of the invention are preferably monoclonal and multivalent, and may be human, humanized or chimeric antibodies, comprising single chain antibodies, Fab fragments, F(ab') fragments, fragments produced by a Fab expression library, and/or binding fragments of any of the above. The term "antibody," as used herein, refers to immunoglobulin molecules and immunologically active portions of immunoglobulin molecules, i.e., molecules that contain at least two antigen binding sites that immunospecifically bind CD3 and CD11b. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. In certain embodiments of the invention, the antibodies are human antigen-binding antibody fragments of the present invention and include, but are not limited to, Fab, Fab' and F(ab')$_2$, Fd, single-chain Fvs (scFv), single-chain antibodies, disulfide-linked Fvs (sdFv) and fragments comprising either a $V_L$ or $V_H$ domain. Antigen-binding antibody fragments, including single-chain antibodies, may comprise the variable region(s) alone or in combination with the entirety or a portion of the following: hinge region, $CH_1$, $CH_2$, $CH_3$ and CL domains. Also included in the invention are antigen-binding fragments comprising any combination of variable region(s) with a hinge region, $CH_1$, $CH_2$, $CH_3$ and CL domains. Preferably, the antibodies are human, murine (e.g., mouse and rat), donkey, sheep, rabbit, goal, guinea pig, camelid, horse, or chicken. As used herein, "human" antibodies include antibodies having the amino acid sequence of a human immunoglobulin and include antibodies isolated from human immunoglobulin libraries, from human B cells, or from animals transgenic for one or more human immunoglobulins.

The antibodies suitable for practicing the methods of the present invention may be bispecific, trispecific or of greater multispecificity. Further, the antibodies of the present invention may have low risk of toxicity against granulocyte (neutrophil), NK cells, and CD4$^+$ cells as bystander cells.

Methods for making bispecific antibodies are known in the art. Traditional production of full length bispecific antibodies is based on the coexpression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al, EMBO J., 10:3655-3659 (1991).

According to another approach described in WO96/27011, the interface between a pair of antibody molecules can be engineered to maximize the percentage of heterodimers which are recovered from recombinant cell culture. Such interfaces may comprise at least a part of the $CH_3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoet-hylamine and is mixed with an equimolar amount of the other Fab'-TNB derivative to form the bispecific antibody. The bispecific antibodies produced can be used as agents for the selective immobilization of enzymes.

Various techniques for making and isolating bispecific antibody fragments directly from recombinant cell culture have also been described. For example, bispecific antibodies have been produced using leucine zippers. Kos-telny et al., J. Immunol, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994). Alternatively, the antibodies can be "linear antibodies" as described in Zapata et al. Protein Eng. 8(10): 1057-1062 (1995). Briefly, these antibodies comprise a pair of tandem Fd segments ($V_H$-$C_{H1}$-$V_H$-$C_H$1) which form a pair of antigen binding regions. Linear antibodies can be bispecific or monospecific.

Multivalent antibodies may be specific for different epitopes of CD133 and EGFRvIII, including, for example, that the multivalent antibodies may bind to one or more of the epitopes present on either CD133 or EGFRvIII. Multivalent antibodies, including bispecific and trispecific antibodies, useful for practicing the present invention are antibodies that immunospecifically bind to both CD133 and EGFRvIII, and may bind one of more additional cancer surface receptors or receptor complexes.

Antibodies useful in the present methods may be described or specified in terms of the particular CDRs they comprise. The invention encompasses the use of an antibody or derivative thereof comprising a heavy or light chain variable domain, said variable domain comprising (a) a set of three CDRs, and (b) a set of four framework regions, and in which said antibody or derivative thereof immunospecifically binds CD133 and EGFRvIII.

Within the context of the present invention, antibodies are understood to include monoclonal antibodies and polyclonal antibodies, antibody fragments (e.g., Fab and F(ab')$_2$), chimeric antibodies bifunctional or bispecific antibodies and tetrameric antibody complexes. Antibodies are understood to be reactive against a selected antigen on the surface of a T cell if they bind with an appropriate affinity (association constant), e.g. greater than or equal to $10^7 M^{-1}$. Additionally, antibodies that may be used in the methods of the present invention may also be described or specified in terms of their binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-9}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, $10^{-15}$ M.

Antibodies can be fragmented using conventional techniques and the fragments screened for utility in the same manner as described above for the whole antibodies. For example, F(ab')$_2$ fragments can be generated by treating antibody with pepsin. The resulting F(ab')$_2$ fragment can be treated to reduce disulfide bridges to produce Fab' fragments The invention also contemplates chimeric antibody derivatives, i.e., antibody molecules that combine a non-human animal variable region and a human constant region. Chimeric antibody molecules can include, for example, the antigen binding domain from an antibody of a mouse, rat, or other species, with human constant regions. A variety of approaches for making chimeric antibodies have been described and can be used to make chimeric antibodies containing the immunoglobulin variable region which recognizes the selected antigens on the surface of differentiated cells or tumor cells. See, for example, Morrison et al., 1985; Proc. Natl. Acad. Sci. U.S.A. 81,6851; Takeda et al., 1985, Nature 314:452; Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B.

Chemical conjugation is based on the use of homo- and heterobifunctional reagents with E-amino groups or hinge region thiol groups. Homobifunctional reagents such as 5,5'-Dithiobis(2-nitrobenzoic acid) (DNTB) generate disulfide bonds between the two Fabs, and 0-phenylenedimaleimide (O-PDM) generate thioether bonds between the two Fabs (Brenner et al., 1985, Glennie et al., 1987). Heterobifunctional reagents such as N-succinimidyl-3-(2-pyridyldito) propionate (SPDP) combine exposed amino groups of antibodies and Fab fragments, regardless of class or isotype (Van Dijk et al., 1989).

The antibodies of the invention, i.e., antibodies that are useful for treating cancers, as well as other cancer comprising cancer stem cells expressing CD133 and EGFRvIII, include derivatives that are modified, i.e., by the covalent attachment of any type of molecule to the antibody such that covalent attachment does not prevent the antibody from binding to CD133 and EGFRvIII. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of turicamycin, etc. Additionally, the derivative may contain one or more non-classical amino acids.

The antibodies may be generated by any suitable method known in the art. Polyclonal antibodies to CD133 and EGFRvIII can be produced by various procedures well known in the art. For example, CD133 or EGFRvIII can be administered to various host animals including, but not limited to, rabbits, mice, rats, etc. to induce the production of sera containing polyclonal antibodies specific for the protein. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed., 1988); Hammer-ling, et al., in: Monoclonal Antibodies and T-Cell Hybrido-mas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Methods for producing and screening for specific antibodies using hybridoma technology are routine and well known in the art.

Antibody fragments which recognize specific epitopes may be generated by known techniques. For example, Fab and F(ab')$_2$ fragments of the invention may be produced by proteolytic cleavage of immunoglobulin molecules, using enzymes such as papain (to produce Fab fragments) or pepsin (to produce F(ab').sub.2 fragments). F(ab')$_2$ fragments contain the variable region, the light chain constant region and the $CH_1$ domain of the heavy chain.

For example, antibodies useful in the methods of the present invention can also be generated using various phage display methods known in the art. In phage display methods, functional antibody domains are displayed on the surface of phage particles which carry the nucleic acid sequences encoding them. In a particular embodiment, such phage can be utilized to display antigen binding domains expressed from a repertoire or combinatorial antibody library (e.g. human or murine). In phage display methods, functional antibody domains are displayed on the surface of phage particles which carry the nucleic acid sequences encoding them. In particular, DNA sequences encoding $V_H$ and $V_L$ domains are amplified from animal cDNA libraries (e.g., human or murine cDNA libraries of lymphoid tissues). The DNA encoding the $V_H$ and $V_L$ domains are recombined together with an scFv linker by PCR and cloned into a phagemid vector (e.g., pCANTAB 6 or pComb 3 HSS). The vector is electroporated in E. coli and the E. coli is infected with helper phage. Phage used in these methods are typically filamentous phage including fd and M13 binding domains expressed from phage with Fab, Fv or disulfide stabilized Fv antibody domains recombinantly fused to either the phage gene III or gene VIII protein. Phage expressing an antigen binding domain that binds to CD133 or EGFRvIII or portions thereof can be selected or identified with antigen e.g., using labeled antigen or antigen bound or captured to a solid surface or bead. Examples of phage display methods that can be used to make the antibodies of the present invention include those disclosed in Brinkman et al, 1995, J. Immunol. Methods 182:41-50; Ames et al, 1995, J. Immunol. Methods 184:177-186; Kettleborough et al, 1994, Eur. J. Immunol. 24:952-958; Persic et al., 1997, Gene 187:9-18; Burton et al., 1994, Advances in Immunology, 191-280; PCT Application No. PCT/GB91/01134; PCT Publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')$_2$ fragments can also be employed using methods known in the art such as those disclosed in PCT publication WO 92/22324; Mullinax et al, BioTechniques 1992, 12(6):864-869; and Sawai et al, 1995, AJRI 34:26-34; and Better et al., 1988, Science 240:1041-1043.

Examples of techniques which can be used to produce single-chain Fvs and antibodies include those described in U.S. Pat. Nos. 4,946,778 and 5,258,498; Huston et al., 1991, Methods in Enzymology 203:46-88; Shu et al., 1993, PNAS 90:7995-7999; and Skerra et al., 1988, Science 240:1038-1040. For some uses, including in vivo use of antibodies in humans and in vitro proliferation or cytotoxicity assays, it is preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science, 1985, 229: 1202; Oi et al, 1986, Bio-Techniques 4:214; Gillies et al., 1989, J. Immunol. Methods 125:191-202; U.S. Pat. Nos. 5,807,715; 4,816,567; and 4,816,397. Humanized antibodies are antibody, molecules from non-human species antibodies that bind the desired antigen having one or more CDRs from the non-human species and framework and constant regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., 1988, Nature 332:323. Antibodies can be humanized using a variety of techniques known in the art including, for example, CDR-grafting (EP 239,400; PCT publication WO 91/09967; U.S. Pat. Nos. 5,225,539; 5,530,101; and 5,585, 089), veneering or resurfacing (EP 592,106; EP 519,596; Padlan, Molecular Immunology, 1991, 28(4/5):489-498; Studnicka et al., 1994, Protein Engineering 7(6):805-814; Roguska. et al, 1994, PNAS 91:969-973), and chain shuffling (U.S. Pat. No. 5,565, 332).

Completely human antibodies are particularly desirable for the therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741.

Human antibodies can also be produced using transgenic mice which express human immunoglobulin genes. For example, the human heavy and light chain immunoglobulin gene complexes may be introduced randomly or by homologous recombination into mouse embryonic stem cells. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of CD133 and EGFRvIII. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see, Lonberg and Huszar, 1995, Int. Rev. Immunol. 13:65-93. For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598. In addition, companies such as Abgenix, Inc. (Freemont, Calif.) and Medarex (Princeton, N.J.) can be engaged to provide human antibodies directed against a selected antigen using technology similar to that described above.

Conditions for Treatment

Cancer, as used herein, refers to hyperproliferative conditions. The term denotes malignant as well as non-malignant cell populations. Such disorders have an excess cell proliferation of one or more subsets of cells, which often appear to differ from the surrounding tissue both morphologically and genotypically. The excess cell proliferation can be determined by reference to the general population and/or by reference to a particular patient, e.g. at an earlier point in the patient's life. Hyperproliferative cell disorders can occur in different types of animals and in humans, and produce different physical manifestations depending upon the affected cells.

Cancers include leukemias, lymphomas (Hodgkins and non-Hodgkins), sarcomas, melanomas, adenomas, carcinomas of solid tissue including breast cancer and pancreatic cancer, hypoxic tumors, squamous cell carcinomas of the mouth, throat, larynx, and lung, genitourinary cancers such as cervical and bladder cancer, hematopoietic cancers, head and neck cancers, and nervous system cancers, benign lesions such as papillomas, and the like. Cancers that form solid tumors, i.e. other than leukemias and lymphomas, are of interest.

Cancers of particular interest are neurologic cancers, including brain tumors. Neurologic tumors are classified according to the kind of cell from which the tumor seems to originate. Diffuse, fibrillary astrocytomas are the most common type of primary brain tumor in adults. These tumors are divided histopathologically into three grades of malignancy: World Health Organization (WHO) grade II astrocytoma, WHO grade III anaplastic astrocytoma and WHO grade IV glioblastoma multiforme (GBM). WHO grade II astocytomas are the most indolent of the diffuse astrocytoma spectrum. Astrocytomas display a remarkable tendency to infiltrate the surrounding brain, confounding therapeutic attempts at local control. These invasive abilities are often apparent in low-grade as well as high-grade tumors.

Glioblastoma multiforme is the most malignant stage of astrocytoma, with survival times of less than 2 years for most patients. Histologically, these tumors are characterized by high proliferation indices, endothelial proliferation and focal necrosis. The highly proliferative nature of these lesions likely results from multiple mitogenic effects. One of the hallmarks of GBM is endothelial proliferation. A host of angiogenic growth factors and their receptors are found in GBMs.

There are biologic subsets of astrocytomas, which may reflect the clinical heterogeneity observed in these tumors. These subsets include brain stem gliomas, which are a form of pediatric diffuse, fibrillary astrocytoma that often follow a malignant course. Brain stem GBMs share genetic features with those adult GBMs that affect younger patients. Pleiomorphic xanthoastrocytoma (PXA) is a superficial, low-grade astrocytic tumor that predominantly affects young adults. While these tumors have a bizarre histological appearance, they are typically slow-growing tumors that may be amenable to surgical cure. Some PXAs, however, may recur as GBM. Pilocytic astrocytoma is the most common astrocytic tumor of childhood and differs clinically and histopathologically from the diffuse, fibrillary astrocytoma that affects adults. Pilocytic astrocytomas do not have the same genomic alterations as diffuse, fibrillary astrocytomas. Subependymal giant cell astrocytomas (SEGA) are periventricular, low-grade astrocytic tumors that are usually associated with tuberous sclerosis (TS), and are histologically identical to the so-called "candle-gutterings" that line the ventricles of TS patients. Similar to the other tumorous lesions in TS, these are slowly-growing and may be more akin to hamartomas than true neoplasms. Desmoplastic cerebral astrocytoma of infancy (DCAI) and desmoplastic infantile ganglioglioma (DIGG) are large, superficial, usually cystic, benign astrocytomas that affect children in the first year or two of life.

Oligodendrogliomas and oligoastrocytomas (mixed gliomas) are diffuse, primarily CNS glial tumors that are clinically and biologically most closely related to the diffuse, fibrillary astrocytomas. The tumors, however, are far less common than astrocytomas and have generally better prognoses than the diffuse astrocytomas. Oligodendrogliomas and oligoastrocytomas may progress, either to WHO grade III anaplastic oligodendroglioma or anaplastic oligoastrocytoma, or to WHO grade IV GBM. Thus, the genetic changes that lead to oligodendroglial tumors constitute yet another pathway to GBM.

Ependymomas are a clinically diverse group of gliomas that vary from aggressive intraventricular tumors of children to benign spinal cord tumors in adults. Transitions of ependymoma to GBM are rare. Choroid plexus tumors are also a varied group of tumors that preferentially occur in the ventricular system, ranging from aggressive supratentorial intraventricular tumors of children to benign cerebellopontine angle tumors of adults. Choroid plexus tumors have been reported occasionally in patients with Li-Fraumeni syndrome and von Hippel-Lindau (VHL) disease.

Medulloblastomas are malignant, primitive tumors that arise in the posterior fossa, primarily in children. These tumors also occur in young adults. Medulloblastomas often are surgically resected with subsequent treatment with chemotherapy and/or radiation. They may recur locally or occasionally as drop metastasis from the posterior fossa to the spine. Meningiomas are common intracranial tumors that arise in the meninges and compress the underlying brain. Although typically considered benign and only rarely frankly malignant, management of these tumors often poses clinical challenges. Histological grades of meningiomas vary with the majority benign, WHO grade I/IV (82%); less commonly atypical, WHO II/IV (15%); and infrequently they occur as anaplastic or malignant, WHO grade III/IV (3%).

Schwannomas are benign tumors that arise on peripheral nerves. Schwannomas may arise on cranial nerves, particularly the vestibular portion of the eighth cranial nerve (vestibular schwannomas, acoustic neuromas) where they present as cerebellopontine angle masses. Hemangioblastomas are tumors of uncertain origin that are composed of endothelial cells, pericytes and so-called stromal cells. These benign tumors most frequently occur in the cerebellum and spinal cord of young adults. Multiple hemangioblastomas are characteristic of von Hippel-Lindau disease (VHL). Hemangiopericytomas (HPCs) are dural tumors which may display locally aggressive behavior and may metastasize. The histogenesis of dural-based hemangiopericytoma (HPC) has long been debated, with some authors classifying it as a distinct entity and others classifying it as a subtype of meningioma.

The symptoms of both primary and metastatic brain tumors often depend on the location in the brain and the size of the tumor. Since various regions of the brain are responsible for specific functions, clinical symptoms will vary a great deal. Tumors in the frontal lobe of the brain may cause weakness and paralysis, mood disturbances, difficulty thinking, confusion and disorientation, and wide emotional mood swings. Parietal lobe tumors may cause seizures, numbness or paralysis, difficulty with handwriting, inability to perform simple mathematical problems, difficulty with certain movements, and loss of the sense of touch. Tumors in the occipital lobe can cause loss of vision in half of each visual field, visual hallucinations, and seizures. Temporal lobe tumors can cause seizures, perceptual and spatial disturbances, and receptive aphasia. If a tumor occurs in the cerebellum, the person may have ataxia, loss of coordination, headaches, and vomiting. Tumors in the hypothalamus may cause emotional changes, and changes in the perception of hot and cold. In addition, hypothalamic tumors may affect growth and nutrition in children. With the exception of the cerebellum, a tumor on one side of the brain causes symptoms and impairment on the opposite side of the body.

Surgery is often used in the treatment of brain tumors to remove or reduce as much of its bulk as possible. By reducing the size of tumor mass, radiotherapy can be more effective. Stereotaxy is a useful adjunct to surgery and radiotherapy (stereotactic radiotherapy). The compositions of the invention may be administered using any medically appropriate procedure, e.g., intravascular (intravenous, intraarterial, intracapillary) administration, injection into the cerebrospinal fluid, intracavity or direct injection in the tumor. Intrathecal administration maybe carried out through the use of an Ommaya reservoir, in accordance with known techniques. (F. Balis et al., Am J. Pediatr. Hematol. Oncol. 11, 74, 76 (1989).

The effective amount of a therapeutic composition to be given to a particular patient will depend on a variety of factors, several of which will be different from patient to patient. Utilizing ordinary skill, the competent clinician will be able to optimize the dosage of a particular therapeutic or imaging composition in the course of routine clinical trials. For the purposes of the present invention, a dose may be contemplated at a dosage range of at least about 0.001, at least about 0.1, at least about 0.5, at least about 1, and not more than about 10, usually not more than about 100 mg/kg.

Agents can be incorporated into a variety of formulations for therapeutic administration by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intracheal, etc., administration. The active agent may be systemic after administration or may be localized by the use of regional administration, intramural administration, or use of an implant that acts to retain the active dose at the site of implantation.

One strategy for drug delivery through the blood brain barrier (BBB) entails disruption of the BBB, either by osmotic means such as mannitol or leukotrienes, or biochemically by the use of vasoactive substances such as bradykinin. The potential for using BBB opening to target specific agents to brain tumors is also an option. A BBB disrupting agent can be co-administered with the therapeutic compositions of the invention when the compositions are administered by intravascular injection. Other strategies to go through the BBB may entail the use of endogenous transport systems, including carrier-mediated transporters such as glucose and amino acid carriers, receptor-mediated transcytosis for insulin or transferrin, and active efflux transporters such as p-glycoprotein. Active transport moieties may also be conjugated to the therapeutic or imaging compounds for use in the invention to facilitate transport across the epithelial wall of the blood vessel. Alternatively, drug delivery behind the BBB is by intrathecal delivery of therapeutics or imaging agents directly to the cranium, as through an Ommaya reservoir.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$ Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with low toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The active ingredient, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The compositions of the invention may be administered using any medically appropriate procedure, e.g., intravascular (intravenous, intraarterial, intracapillary) administration, injection into the cerebrospinal fluid, intracavity or direct injection in the tumor. Intrathecal administration maybe carried out through the use of an Ommaya reservoir, in accordance with known techniques. (F. Balis et al., Am J. Pediatr. Hematol. Oncol. 11,74,76 (1989). For the imaging compositions of the invention, administration via intravascular injection is preferred for pre-operative visualization of the tumor. Post-operative visualization or visualization concurrent with an operation may be through intrathecal or intracavity administration, as through an Ommaya reservoir, or also by intravascular administration.

Where the therapeutic agents are administered in combination with treatment of brain tumors, one method for administration of the therapeutic compositions of the invention is by deposition into or near the tumor by any suitable technique, such as by direct injection (aided by stereotaxic positioning of an injection syringe, if necessary) or by placing the tip of an Ommaya reservoir into a cavity, or cyst, for administration. Alternatively, a convection-enhanced delivery catheter may be implanted directly into the tumor mass, into a natural or surgically created cyst, or into the normal brain mass. Such convection-enhanced pharmaceutical composition delivery devices greatly improve the diffusion of the composition throughout the brain mass. The implanted catheters of these delivery devices utilize highflow microinfusion (with flow rates in the range of about 0.5 to 15.0 .mu.l/minute), rather than diffusive flow, to deliver the therapeutic composition to the brain and/or tumor mass. Such devices are described in U.S. Pat. No. 5,720,720, incorporated fully herein by reference.

The compositions can be administered to the subject in a series of more than one administration. For therapeutic compositions, regular periodic administration will sometimes be required, or may be desirable. Therapeutic regimens will vary with the agent, e.g. daily or semi-daily basis; administered for more defined time courses, e.g. one, two three or more days, one or more weeks, one or more months, etc., taken daily, semi-daily, semiweekly, weekly, etc.

Formulations may be optimized for retention and stabilization in the brain. When the agent is administered into the cranial compartment, it is desirable for the agent to be retained in the compartment, and not to diffuse or otherwise cross the blood brain barrier. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the agent in a biodegradable or bioerodible implant. The rate of release of the therapeutically active agent is controlled by the rate of transport through the polymeric matrix, and the biodegradation of the implant. The transport of drug through the polymer barrier will also be affected by compound solubility, polymer hydrophilicity, extent of polymer crosslinking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

The implants may be monolithic, i.e. having the active agent homogenously distributed through the polymeric matrix, or encapsulated, where a reservoir of active agent is encapsulated by the polymeric matrix. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, ease of encapsulation, a half-life in the physiological environment.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxy-aliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the subject invention. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137-149.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

Cancer Stem Cells

In one embodiment of the invention, a biologic sample from a cancer patient, e.g. a patient suffering from a cancer as described above, is stained with reagents specific for CD133 and EGFRvIII. The analysis of staining patterns provides the relative distribution of cancer stem cells, which distribution predicts the tumorigenicity of the cancer.

In one embodiment, the patient sample is compared to a control, or a standard test value. In another embodiment, the patient sample is compared to a pre-cancerous sample, or to one or more time points through the course of the disease.

The information thus derived is useful in prognosis and diagnosis, including susceptibility to acceleration of disease, status of a diseased state and response to changes in the environment, such as the passage of time, treatment with drugs or other modalities. The cells can also be classified as to their ability to respond to therapeutic agents and treatments, isolated for research purposes, screened for gene expression, and the like. The clinical samples can be further characterized by genetic analysis, proteomics, cell surface staining, or other means, in order to determine the presence of markers that are useful in classification. For example, genetic abnormalities can be causative of disease susceptibility or drug responsiveness, or can be linked to such phenotypes.

Differential Cell Analysis

The presence of CSC in a patient sample can be indicative of the stage of a cancer. In addition, detection of CSC can be used to monitor response to therapy and to aid in prognosis. The presence of CSC can be determined by quantitating the cells having the phenotype of the CSC described herein.

In addition to cell surface phenotyping, it is useful to quantitate the cells in a sample that have a "stem cell" character. This can be determined by determining the ability of the cells to self-renew and proliferate in culture, e.g. in forming neurospheres. Alternatively the cells can be tested for tumorigenicity in an animal model.

Clinical samples for use in the methods of the invention may be obtained from a variety of sources, particularly biopsy sample, although in some instances samples such as cerebrospinal fluid and the like may be used. Such samples can be separated by centrifugation, elutriation, density gradient separation, apheresis, affinity selection, panning, FACS, centrifugation with Hypaque, etc. prior to analysis. Once a sample is obtained, it can be used directly, frozen, or maintained in appropriate culture medium for short periods of time. Various media can be employed to maintain cells. The samples may be obtained by any convenient procedure, such as the biopsy, or the like. Usually a sample will comprise at least about $10^2$ cells, more usually at least about $10^3$ cells, and preferable $10^4$, $10^5$ or more cells. Typically the samples will be from human patients, although animal models may find use, e.g. equine, bovine, porcine, canine, feline, rodent, e.g. mice, rats, hamster, primate, etc.

The labeled cells are quantitated as to the expression of cell surface markers. It is particularly convenient in a clinical setting to perform the immunoassay in a self-contained apparatus. A number of such methods are known in the art. The apparatus will generally employ a continuous flow-path of a suitable filter or membrane, having at least three regions, a fluid transport region, a sample region, and a measuring region. The sample region is prevented from fluid transfer contact with the other portions of the flow path prior to receiving the sample. After the sample region receives the sample, it is brought into fluid transfer relationship with the other regions, and the fluid transfer region contacted with fluid to permit a reagent solution to pass through the sample region and into the measuring region. The measuring region may have bound to it a conjugate of an enzyme with progenitor cell specific antibodies.

The comparison of a differential progenitor analysis obtained from a patient sample, and a reference differential progenitor analysis is accomplished by the use of suitable deduction protocols, AI systems, statistical comparisons, etc. A comparison with a reference differential progenitor analysis from normal cells, cells from similarly diseased tissue, and the like, can provide an indication of the disease staging. A database of reference differential progenitor analyses can be compiled. An analysis of particular interest tracks a patient, e.g. in the chronic and pre-leukemic stages of disease, such that acceleration of disease is observed at an early stage. The methods of the invention provide detection of acceleration prior to onset of clinical symptoms, and therefore allow early therapeutic intervention, e.g. initiation of chemotherapy, increase of chemotherapy dose, changing selection of chemotherapeutic drug, and the like.

Cell Surface Staining Methods

Analysis by cell staining may use conventional methods, as known in the art. Techniques providing accurate enumeration include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide).

The affinity reagents may be specific receptors or ligands for the cell surface molecules indicated above. In addition to antibody reagents, peptide-MHC antigen and T cell receptor pairs may be used; peptide ligands and receptor; effector and receptor molecules, and the like. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

Of particular interest is the use of antibodies as affinity reagents. Conveniently, these antibodies are conjugated with a label for use in separation. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker.

The antibodies are added to a suspension of cells, and incubated for a period of time sufficient to bind the available cell surface antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated will be any medium that maintains the viability of the cells. A preferred medium is phosphate buffered saline containing from 0.1 to 0.5% BSA. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, etc.

The labeled cells are then quantitated as to the expression of cell surface markers as previously described. It is particularly convenient in a clinical setting to perform the immunoassay in a self-contained apparatus. A number of such methods are known in the art. The apparatus will generally employ a continuous flow-path of a suitable filter or membrane, having at least three regions, a fluid transport region, a sample region, and a measuring region. The sample region is prevented from fluid transfer contact with the other portions of the flow path prior to receiving the sample. After the sample region receives the sample, it is brought into fluid transfer relationship with the other regions, and the fluid transfer region contacted with fluid to permit a reagent solution to pass through the sample region and into the measuring region. The measuring region may have bound to it a conjugate of an enzyme with progenitor cell specific antibodies.

CSC Compositions

The cells of interest may be separated from a complex mixture of cells by techniques that enrich for cells having the above described characteristics. For isolation of cells from tissue, an appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

Compositions highly enriched for CSC are achieved in this manner. The subject population may be at or about 50% or more of the cell composition, and preferably be at or about 75% or more of the cell composition, and may be 90% or more. The desired cells are identified by their surface phenotype, by the ability to self-renew, an essential property of stem cells. The enriched cell population may be used immediately, or may be frozen at liquid nitrogen temperatures and stored for long periods of time, being thawed and capable of being reused. The cells will usually be stored in 10% DMSO, 50% FCS, 40% RPMI 1640 medium. The population of cells enriched for CSC may be used in a variety of screening assays and cultures, as described below.

The enriched CSC population may be grown in vitro under various culture conditions. Culture medium may be liquid or semi-solid, e.g. containing agar, methylcellulose, etc. The cell population may be conveniently suspended in an appropriate nutrient medium, such as Iscove's modified DMEM or RPMI-1640, normally supplemented with fetal calf serum (about 5-10%), L-glutamine, a thiol, particularly 2-mercaptoethanol, and antibiotics, e.g. penicillin and streptomycin.

The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. A wide variety of growth factors may be used in culturing the cells, e.g. LIF, steel factor (c-kit ligand), EGF, insulin, IGF, NGF, etc. In addition to, or instead of growth factors, the subject cells may be grown in a co-culture with fibroblasts, stromal or other feeder layer cells.

The comparison of a differential progenitor analysis; or a CSC analysis obtained from a patient sample, and a reference analysis is accomplished by the use of suitable deduction protocols, artificial intelligence (AI) systems, statistical comparisons, etc. A comparison with a reference differential progenitor analysis from normal cells, cells from similarly diseased tissue, and the like, can provide an indication of the disease staging. A database of reference differential progenitor analyses can be compiled. An analysis of particular interest tracks a patient, e.g. in the chronic and pre-leukemic stages of disease, such that acceleration of disease is observed at an early stage. The methods of the invention provide detection of acceleration prior to onset of clinical symptoms, and therefore allow early therapeutic intervention, e.g. initiation of chemotherapy, increase of chemotherapy dose, changing selection of chemotherapeutic drug, and the like.

Screening Assays

CSC are also useful for in vitro assays and screening to detect factors and chemotherapeutic agents that are active on cancer stem cells. Of particular interest are screening assays for agents that are active on human cells. A wide variety of assays may be used for this purpose, including immunoassays for protein binding; determination of cell growth, differentiation and functional activity; production of factors; and the like.

In screening assays for biologically active agents, antiproliferative drugs; etc. the CSC composition, usually a culture comprising CSC, is contacted with the agent of interest, and the effect of the agent assessed by monitoring output parameters, such as expression of markers, cell viability, and the like. The cells may be freshly isolated, cultured, genetically altered as described above to provide a marker for activation of signaling pathways, and the like. The cells may be environmentally induced variants of clonal cultures: e.g. split into independent cultures and grown under distinct conditions, for example with or without drugs; in the presence or absence of cytokines or combinations thereof. The manner in which cells respond to an agent, particularly a pharmacologic agent, including the timing of responses, is an important reflection of the physiologic state of the cell.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

Agents of interest for screening include known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like.

In addition to complex biological agents candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

Test compounds include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

The term samples also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1 µl to 1 ml of a biological sample is sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents are screened for biological activity by adding the agent to at least one and usually a plurality of cell samples, usually in conjunction with cells lacking the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the presence of the selected markers. For measuring the amount of a molecule that is present, a convenient method is to label a molecule with a detectable moiety, which may be fluorescent, luminescent, radioactive, enzymatically active, etc., particularly a molecule specific for binding to the parameter with high affinity. Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells. (for a review see Jones et al. (1999) Trends Biotechnol. 17(12):477-81). Thus, antibodies can be genetically modified to provide a fluorescent dye as part of their structure. Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman et al. (1999) Biotechniques 26(1):112-225; Kawamoto et al. (1999) Genome Res 9(12):1305-12; and Chen et al. (1998) Genomics 51(3):313-24, for examples.

Kits may be provided, where the kit will comprise a staining reagents that are sufficient to differentially identify the NCSC. A marker combination of interest may include CD133 and EGFRvIII. The staining reagents are preferably antibodies, and may be detectably labeled. Kits may also include tubes, buffers, etc., and instructions for use.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

EXPERIMENTAL

Example 1

Despite advances in our understanding the overall median survival for glioblastoma multiforme (GBM) remains at 11-13 months with almost 100% recurrence. Recently, there has been considerable interest in the cancer stem cell (CSC) hypothesis which states that neoplastic clones are initiated and maintained exclusively by a small fraction of cells with stem cell properties. A corollary is that their incomplete removal is a primary basis for relapse. To specifically target brain tumor stem cells, it is desirable to employ a marker specific for both tumors and stem cells. Multiple laboratories have demonstrated that CD133+ population is a major tumor initiating population; unfortunately, developing therapies solely using CD133 would also target neural and hematopoietic stem cells. A tumor specific genetic alteration of the EGF receptor, EGFRvIII, is commonly present in many solid tumors, making it an ideal antigen for targeted therapies.

In this study we wished to analyze whether EGFRvIII is expressed in brain tumor CSC, and if so explore its role in tumor initiation and maintenance. Freshly resected tumors were dissociated using a protocol to preserve cell surface makers. Cells were then co-sorted for CD133 and EGFRvIII. We found EGFRvIII expression in a significant fraction (70±8%, n=8) of the CD133+ population. In order to explore the role of EGFRvIII in the CSC population we developed conditions for isolation and long term (>90 days) growth of tumor spheres from primary brain tumors and successfully isolated and expanded tumor spheres from 11 GBM's, 1 ependymoma, 2 medulloblastomas and 1 atypical tetroid/rhabdoid tumor. All of the dissociated primary tumor spheres exhibited the capacity to form secondary tumor spheres, demonstrating an ability to self-renew. Furthermore, using an in-vitro limiting dilution assay we show that EGFRvIII+/CD133+ cells from GBM tumors (n=3) have at least a 2 fold higher propensity to form clonal spheres as compared to the presence of EGFRvIII or CD133 alone. Previous experiments in many laboratories have shown that expression of EGFRvIII is rapidly lost when brain tumors are cultured in a serum based media. Here we show the maintenance of EGFRvIII expression for up to 3 months in tumor spheres grown in a serum free "stem cell" growth media. Overall, 8 of 11 GBM derived neurospheres were positive for EGFRvIII, as well as 1 of 1 ependymoma, 1 of 2 medulloblastoma and 1 of 1 AT/RT. To verify that the tumor sphere population was indeed an enriched "stem-cell" population, we used standard western blotting and RT-PCR techniques to verify co-expression of EGFRvIII with three stem cell markers (CD133, Sox2, and Nestin). Additionally, EGFRvIII expression is lost when tumor spheres are exposed to differentiation conditions (serum, NT3, BMP, BDNF & GDNF), suggesting a preferential expression of EGFRvIII in tumors stem cells. These data taken together suggest that EGFRvIII is frequently expressed in brain tumor stem cells, is associated with the tumor initiating fraction and the expression of EGFRvIII may be regulated by state of differentiation of the tumor.

Co-Expression of EGFRvIII and CD133 in Primary Glioblastoma Tumors.

Experiments were initiated to see if CD133 and EGFRvIII are co-expressed in glioblastoma. Samples that were EGFRvIII positive that were then FACS sorted for CD133 and EGFRvIII following 2-3 days of culture. In some cases, the $CD133^+EGFRvIII^+$ double positive population is a significant fraction of either the CD133 and/or EGFRvIII positive cells. This indicates that CD133 and EGFRvIII is indeed co-expressed in glioblastoma.

Tumors that express EGFRvIII rapidly lose expression once placed in culture. To avoid cell culture, a dissociation protocol was developed that uses no non-specific proteases and was found to not significantly alter cell surface markers after dissociation. Using this improved protocol, we found a significant fraction of cells that were CD133$^+$/EGFRvIII$^+$ double positive, and interestingly these cells was the majority of either population (GBM6).

Propagation of Cancer Stem Cells from Glioblastoma Tumors Preserves EGFRvIII expression.

Next, we began isolating CSCs from glioblastomas. Conditions for the successful isolation of individual cells from primary tumors were established and the cells were then cultured in a defined serum-free media that favors the growth of tumor spheres; similar conditions have been used to grow neurospheres and cancer stem cells from brain tumors.

Since previous published studies on tumor spheres from GBMs did not analyze EGFRvIII expression, we analyzed our spheres for its expression. Tumor spheres from one primary sample that had high levels of expression of EGFRvIII showed similarly high levels after 3 weeks of passage. This was highly interesting given that no GBM in culture had previously been reported to maintain EGFRvIII expression, and further confirming that tumor spheres do correspond to the CSC population. We then analyzed a specimen that showed no EGFRvIII expression by Western blot analysis and less than 1% CD133$^+$/EGFRvIII$^+$ double positive cells. Surprisingly, these tumor spheres did show expression of EGFRvIII demonstrating that the CSC in the tumor did contain EGFRvIII, which was subsequently enriched in culture. We have analyzed tumor spheres derived from 14 tumors. 11/14 tumors spheres were positive for EGFRvIII expression. Experiments are underway to verify that the CD133$^+$/EGFRvIII$^+$ double positive population has enhanced tumorigenicity as compared to either the CD133$^+$ or EGFRvIII$^+$ population alone when injected into NOD-SCID mice.

Generation of a Bispecific Antibody Against CD133 and EGFRvIII.

We obtained a hybridoma against CD133 (AC133.1), and EGFRvIII and used these to isolate the $V_H$ and $V_L$ regions using PCR. These were first cloned into the pAK400 vector for the production of scFv. We then tested the affinity of the purified scFv towards their respective antigens. To test the scFv against EGFRvIII, the EGFRvIII peptide was bound to 96 well plates. As a negative control, BSA alone was bound to the wells. Various concentrations of scFv or monoclonal antibody to EGFRvIII were tested. This revealed that the scFv-EGFRvIII had an apparent affinity very similar to that of a monoclonal antibody against EGFRvIII and had virtually no binding to BSA alone. For comparison, we also tested the scFv against CD133 which showed no specific binding to the EGFRvIII peptide.

Similar experiments were performed for the scFv against CD133. For the source of antigen, we prepared the membrane fraction from Caco-2 cells, which are known to express a high level of CD133. This showed that the scFv-CD133 had a high affinity but was approximately 3 fold lower than the monoclonal antibody from which the scFv was derived, which is expected since the scFv is not bivalent, unlike the monoclonal antibody The scFv-EGFRvIII showed no binding in this assay.

Expression, and Purification of the Bispecific Antibody Against EGFRvIII and CD133.

Figure 1B:
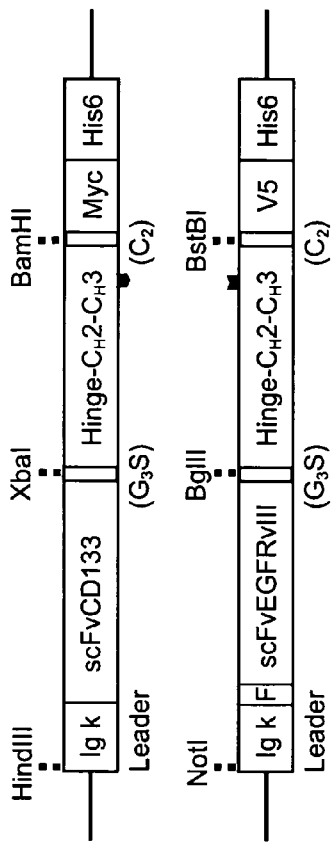
Figure 1C:
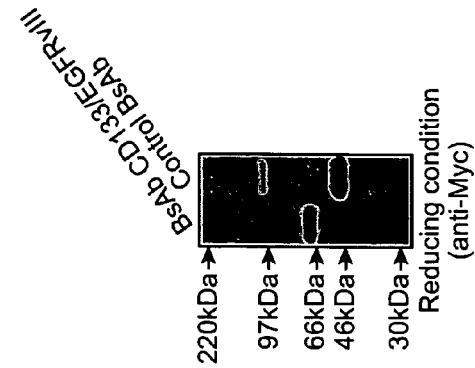
Figure 1D:
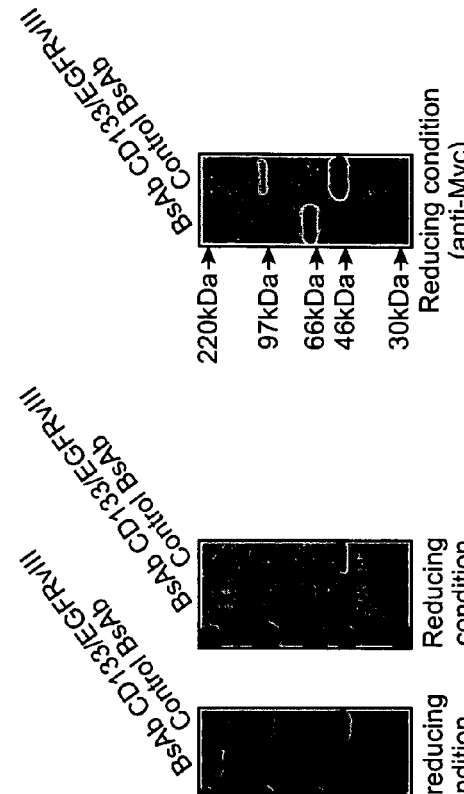
Figure 1E:
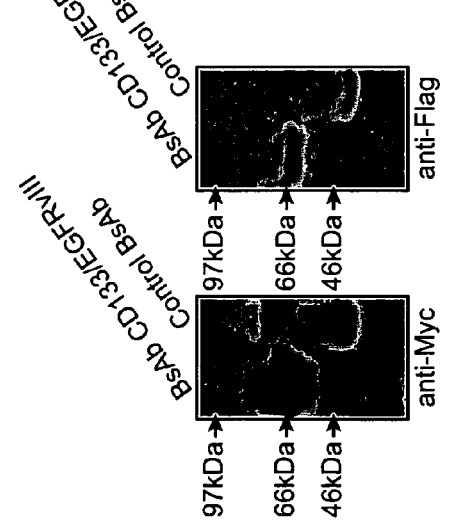
Figure 2:
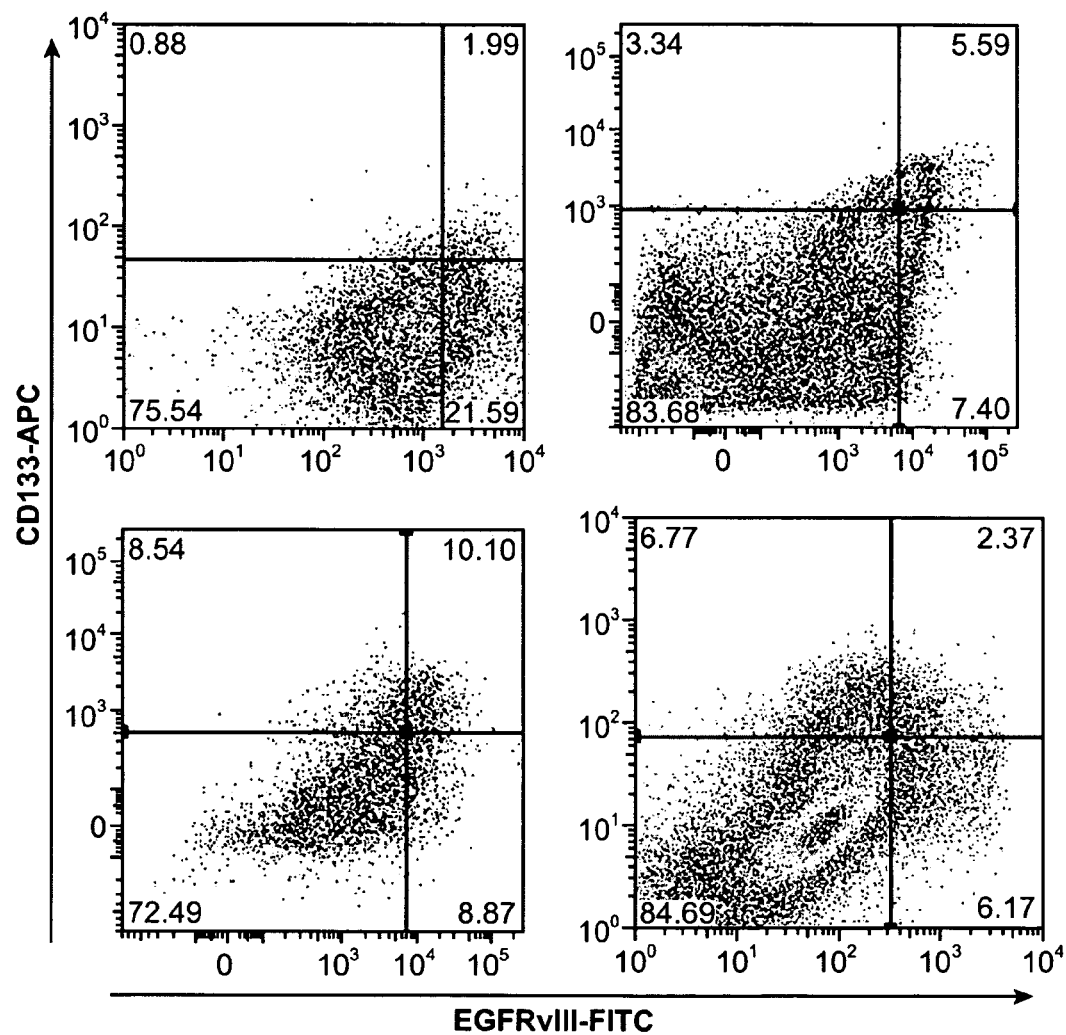
FIG. 2: Freshly resected human GBM samples were dissociated using a collagenase based medium and analysed using flow cytometry for expression of CD133 and EGFRvIII. The anti-CD133 antibody was recognized with an antibody conjugated to allophycoerythrin (APC) and the anti-EGFRvIII antibody was recognized with an antibody conjugated to FITC. Shown here are representative plots of four tumors which distinctly show the heterogeneity in cell type as well as protein expression. The percentage of cells in each quadrant is shown.

These scFvs were then cloned into the pBudCE4.1 bicistronic expression vector and then transfected into HEK293 cells. The $CH_2$-$CH_3$ region of each scFv has a "knob into hole" design to drive the formation of heteromers. FIG. 1A is a diagram of the construct used for each scFv and FIG. 1B shows the expected structure of the bispecific antibody. We verified that this bicistronic vector did indeed express each scFv using anti-Myc antibody to detect the scFv-CD133 portion and anti-Flag antibody to detect the scFv-EGFRvIII (FIG. 1C). This revealed expression of the expected 66 kDa band. As a positive control, we used a bispecific antibody construct which showed expression of the expected 46 kDa scFv (this vector lacks the CH2 and hinge region resulting in a 46 kDa protein). We then derived cell lines with stable expression of this construct and used Ni-NTA affinity chromatography to isolate these proteins. In FIG. 1D, we show that under non-reducing conditions we are able to isolate a protein of ~170 kDa which corresponds to the expected size for a dimeric bispecific antibody. We reconfirmed that this was indeed composed of the respective scFvs (FIG. 1E, only the scFv-CD133 is shown here). Gel filtration experiments is done to confirm that this molecule is a heteromer composed of the two scFvs.

Confirmation of Specificity of the Bispecific Antibody Against EGFRvIII and CD133.

Affinities for the BsAb, a non-specific antibody (Her2/CD16 scFv BsAb), the recombinant anti-EGFRvIII and anti-CD133 are determined by surface plasmon resonance Biacore analysis. Chips will contain either CD133 protein or EGFRvIII peptide or both. For comparative purposes across experiments, we will strive to bind precise equimolar amounts of each target antigen to the chip. To demonstrate that the BsAb has increased affinity when both target antigens are present, chips are used that contain both proteins in different molar ratios. While this is not a direct measure of affinity per se because the target is a complex mixture, one can calculate an apparent affinity.

A two-step sandwich binding assay is performed to determine whether the BsAb can bind to both of its targets simultaneously. The BsAb is passed over a sensor chip containing a high density of the EGFRvIII peptide. Once binding is observed, the CD133 protein is passed over the same (unwashed) flow cell, and a change in response recorded. As a negative control, an unrelated protein is used, and any change in response recorded.

Further in-vitro experiments are carried out on tumor spheres obtained from double sorting of CD133 and EGFRvIII. This will give populations that have both the two target epitopes, either epitopes or none at all, giving internal controls from within the same sample. We will determine if the BsAb is effective at a lower concentrations than the recombinant anti-EGFRvIII or anti-CD133 alone in inhibiting tumor sphere formation. Each recombinant antibody is used in tumor sphere experiments over 1000 fold concentration range, and the $EC_{50}$ dose determined.

Effectiveness of the BsAb in Inhibiting Tumor Spheres.

It is determined what amounts of the BsAb are necessary, and how best to mediate cell killing. To avoid wasting primary tumor samples or undue animal experimentation pilot experiments are performed on cell lines. A drawback of all glioblastoma cell lines in culture is that they lose expression of EGFRvIII while maintaining expression of CD133 in culture. To avoid these problems, a cell line is created that expresses both markers, using established malignant glioma derived cell lines, specifically U87 and T98G, and transfect them with EGFRvIII and CD133 at varying ratios. This allows control cell surface expression stochiometries of EGFRvIII and CD133.

Ability of the BsAb to induce ADCC in target cells (heterologous as well as primary cells) expressing the same permutation of epitopes will be carried out using a standard Chr-51 release assay using a similar concentration range. After the parameters are known, tumor cells isolated from patients are used. Tumors are dissociated and then frozen (since this does not affect viability or surface marker expression) while being tested for EGFRvIII expression. Tumors that are EGFRvIII positive are used for subsequent studies.

ADCC on Isolated Tumor Spheres:

When cultured in stem cell media, the bulk of tumor cells form a monolayer but a hallmark of CSCs is the ability to form "tumor spheres" that can self renew. These spheres are akin to the neurospheres that neural stem cells form. Tumor spheres, unlike the bulk of tumor cells, maintain the genetic and phenotypic expression patterns seen in the original tumor. Tumors are sorted for four populations, $CD133^+/EGFRvIII^+$, $CD133^+/EGFRvIII^-$, $CD133^-/EGFRvIII^+$, and $CD133^-/EGFRvIII^-$ using flow cytometry with confirmation by western blot analysis. Sorted cells are tested in parallel for tumorigenicity by serial dilution as well as serial transplantation in NOD-SCID mice. These 4 populations are propagated in culture as tumor spheres where the efficiency of sphere formation as a percentage of cells seeded is calculated. These populations are then subjected to a standard Chr-51 release assay to determine specificity and targeting of surface epitope presentation of EGFRvIII and CD133.

Test the Effectiveness of the Bispecific Antibody in Inhibiting Tumor Formation In Vivo.

Dissociated tumor cells are treated with the BsAb as described above using the concentration of antibody that produces 50% inhibition of tumor sphere formation. Mice are injected with 200,000 cells (a dose that produces engraftment in >90% of mice) to see if there is an impairment in tumor take. With 5 mice per group and 4 antibodies to evaluate, ~20-40 animals are used per tumor.

Cells are sorted to obtain the $CD133^+/EGFRvIII^+$ cells, treated with each antibody and injected at a concentration of $10^3$ cells. An estimated 20-40 animals are used per tumor.

For brain tumors, several studies have indicated that it is highly prevalent on GBMs, and pediatric gliomas and medulloblastomas. As such, once this agent is developed it can be useful for a high percentage of brain tumors, and may be adapted for other cancers that express EGFRvIII, such as breast and colon where both EGFRvIII and CD133 have been shown to express.

Methods:

Creation of a $CD133^+/EGFRvIII^+$ Positive Control Cell Line.

A $CD133^+/EGFRvIII^+$ cell line is created by transfecting U87 and T98G cell lines with EGFRvIII and CD133 using standard transfection protocols. Clones with varying expression levels are isolated and characterized. Expression levels chosen are at a similar range as seen in GBM derived CSCs.

Effective Antibody Concentration Range.

$5\times10^3$ of $CD133^+/EGFRvIII^+$ cells in a 96 well format are incubated with varying concentrations of BsAb or non-specific BsAb and 15% human plasma (as the source of complement) and human PBMCs at an effector to target ratio of 50:1. Following incubation for 3 h at 37 C., cell lysis is quantitated using chromium release assay as has been previously described. Because non-specific cell killing may be seen due to random binding, we will use concentrations of BsAb with at least 5× greater efficiency than the non-specific BsAb.

Studies on Primary Tumors.

Cells are dissociated using a collagenase based protocol. More than 50% of the dissociated cells are frozen down for future analysis. The remainder are sorted for the 4 populations mentioned above, and further divided for a) cranial injections into mice to determine tumorigenicity and b) plated in defined serum free media for tumor sphere formation. IHC and western blot are performed on the primary sample to determine expression of EGFRvIII. Nestin, GFAP and MAP2 staining are used to confirm the character of the tumor spheres.

Tumor Sphere Analysis.

The 4 sorted populations are plated according to the need of the experiment. For a limiting dilution analysis cells are plated in graded dilutions of the cell suspension in a 96 well plate and number of well with spheres counted at the end of the experiment. $2\times10^6$ cells are left untreated or incubated with various concentrations of a BsAb or recombinant antibody plus 15% plasma and $1\times10^7$ effector cells in 1 ml for 2 h at 37 C. Cells are diluted into 10 ml. of stem cell media and seeded into 60 mm dishes and allowed to grow for 2 weeks. The PBMCs should die within several days, but preliminary experiments will be conducted to confirm that they do not interfere with tumor sphere formation.

Tumor Engraftment in NOD-SCID Mice.

Cells are stereotactically injected into the frontal cortex of 6 week old NOD-SCID mice. Cells are injected in a final volume of 5 µl using a Hamilton syringe. NOD-SCID Mice are injected with cells sorted into the 4 previously described populations. The antibodies are injected i.p. at various time points. These animals are monitored and days to death noted or otherwise sacrificed at 8-10 weeks.

Example 2

EGFRvIII is Expressed in a Significant Fraction of CD133+ Glioblastoma Cells

Singh et al (2004) showed that CD133+ glioma cells are the tumor initiating cells and are composed of anywhere between 0.5 to 30% of the tumor. Because EGFRvIII is the result of a gene rearrangement in glioblastoma tumors, and the cancer stem cell theory postulates that genetic alterations are resident in CSCs, we sought evidence that EGFRvIII is co-expressed with CD133. Using a modified dissociation protocol we analyzed co-expression using flow cytometry (Table-1). FIG. 1 show the FACS plots from 4 different GBM surgically resected on different days. The total EGFRvIII expression varied from 1.5% to 23% and total CD133 expression was from 1.9% to 18%. Interestingly, the fraction of cells that were EGFRvIII+/CD133+ was a significant fraction of the total CD133 population (average of 71.77%). These results demonstrate that EGFRvIII is highly co-expressed with CD133.

Generation of Single Chain Variable Fragment for CD133 and EGFRvIII.

The previous data suggested that EGFRvIII could be used for strategies that target CSC. We noted, though, that there was a significant fraction of cells, from 18.9% to 90%, that were EGFRvIII+ but CD133−. This could presumably be due to differentiation of the CSC into less tumorigenic progenitor cells. The presence of such a large EGFRvIII+/CD133− population would complicate strategies that only target EGFRvIII because this excess population of cells would hinder targeting of the EGFRvIII+/CD133+, the population that would more correspond to the true CSC. To efficiently and selectively target tumor initiating cells, we explored a bispecific antibody strategy to target cells expressing both antigens. The generation of a scFv against EGFRvIII has been previously described (Beers et al. (2000) Clin Cancer Res 6, 2835-2843). We synthesized the $V_H$ and $V_L$ region and subcloned it into a bacterial expression vector (pET32) to generate the scFv-EGFRvIII. To obtain a scFv against CD133, we used the AC133 hybridoma cell line and obtained the $V_H$ and $V_L$ region by RT-PCR amplification from mRNA extracted from the hybridoma. These individual fragments were assembled together using SOE-PCR and subcloned into the pAK100 phagemid and then subsequently subcloned into pET32 for expression and protein purification.

Figure 3A:
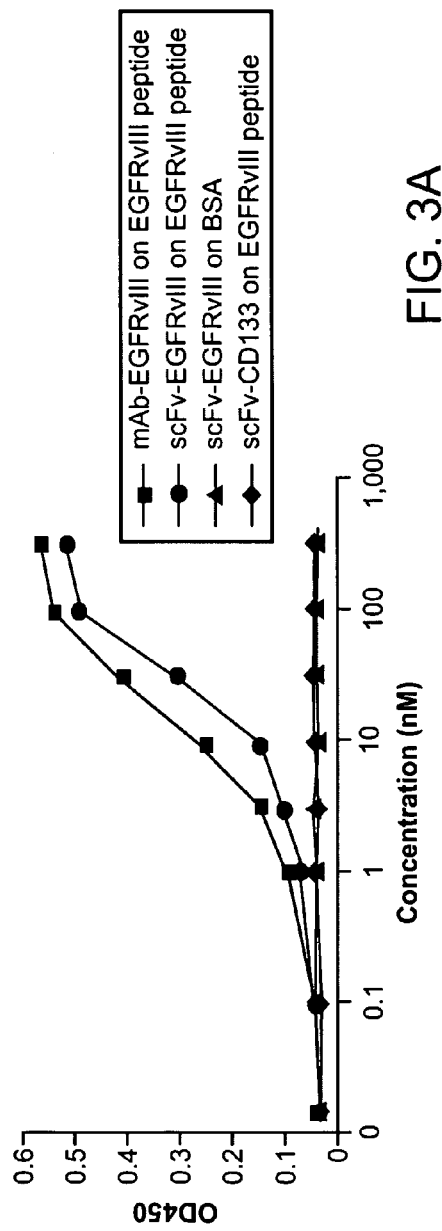
FIG. 3: Affinity analysis of individual scFv chains. (A) Binding affinity of scFv-EGFRvIII to the EGFRvIII junctional peptide was compared to a monoclonal anti-EGFRvIII antibody. ScFv-EGFRvIII has a $K_D=28$ nm as compared to a $K_D=20$ nm of the monoclonal anti-EGFRvIII antibody. ScFv-AC133 showed very little binding to the EGFRvIII junctional peptide. (B) Since the epitope of the anti-CD133 clone (AC133) is not well defined but is known to be glycosylated we used membrane fraction of Caco-2 cells as the antigen to test the binding affinity of scFv-AC133. The relative binding affinity of scFv-AC133 ($K_D=155$ nm) was 2-fold lower than anti-CD133 monoclonal antibody ($K_D=83$ nm) where as scFv-EGFRvIII showed no binding to the Caco-2 membrane fraction.
Figure 3B:
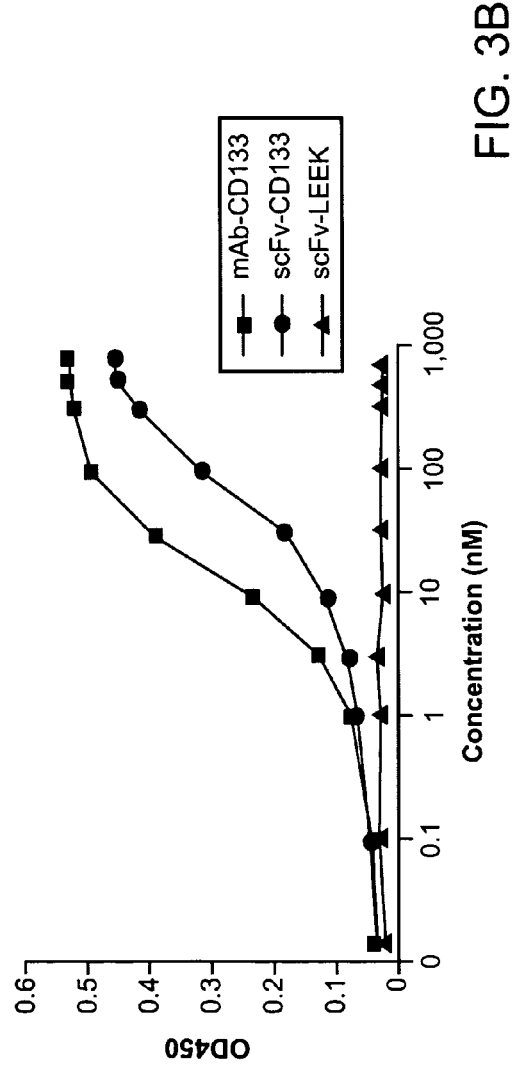

To determine the individual specificities we used an ELISA based binding affinity assay. For scFv-EGFRvIII we coated plates with the peptide that encompasses the junction of Exon 1 and Exon 8. As shown in FIG. 3, the scFv-EGFRvIII had a high affinity ($K_D$=28 nm) for the EGFRvIII peptide and was very similar in affinity to that of a mouse monoclonal antibody towards EGFRvIII ($K_D$=20 nm). As controls, the scFv-EGFRvIII did not show any binding to increasing concentration of BSA and as a further control we used the scFv-AC133 which did not show any binding to the EGFRvIII junctional peptide. To determine the affinity of scFv-AC133, because the epitope for CD133 is not clearly defined but is known to be glycosylated we used the plasma membrane fraction of Caco-2 cells as antigen and carried out the ELISA assay. The relative equilibrium constant (KD) of scFv-AC133 was 155 nM as compared to 83 nM for the AC133 mouse monoclonal antibody purified from hybridoma. We did not observe any binding of scFv-EGFRvIII to Caco-2 membrane fractions, demonstrating that the scFv chains isolated had specific affinities for their respective antigens only.

Figure 4A:
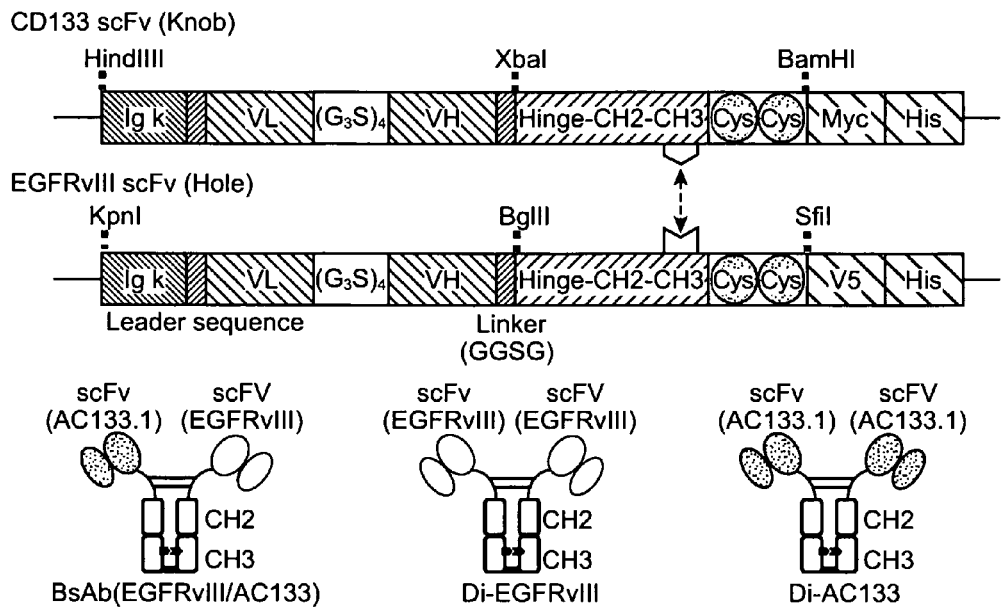
FIG. 4: (A) Schematic of the Bispecific antibody showing the scFv chains of anti-CD133 and anti-EGFRvIII. The two chains are expressed in HEK293 cells using a bicistronic expression vector. Dimerization of the two chains is achieved by a knob-inot-hole configuration. Monospecific dimeric minibodies were developed as controls (lower panel). (B) The minibodies are secreted into the media presence of both chains is verified by western blot. Analysis of the minibody under nonreducing and reducing conditions confirms the presence of the dimeric form of the BsAb. Purification of the BsAb using a IMAC column and subsequent detection using anti-myc tag confirms the presence of purified BsAb. As control we used a previously described anti-HER2/neu-anti-CD16 bispecific minibody. (C) the presence of both the chains on a single minibody was confirmed by immunoprecipitation of the minibody using anti-myc agarose and subsequent western blot with anti-V5 antibody.
Figure 4B:
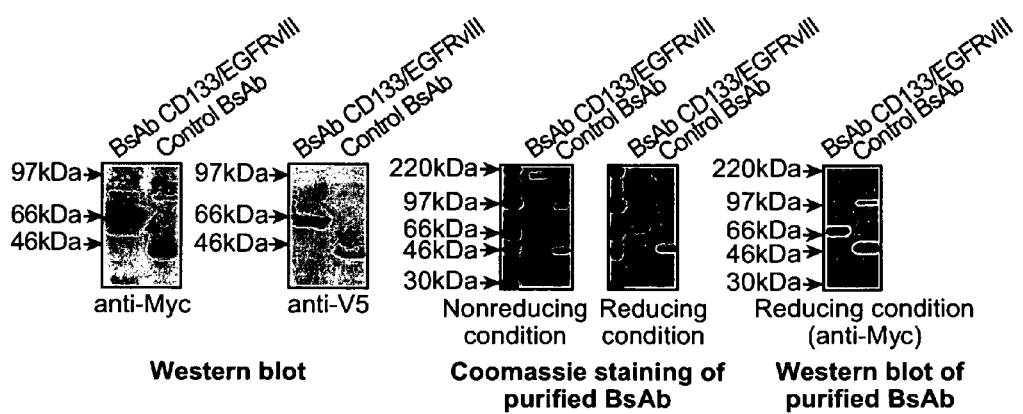
Figure 4C:
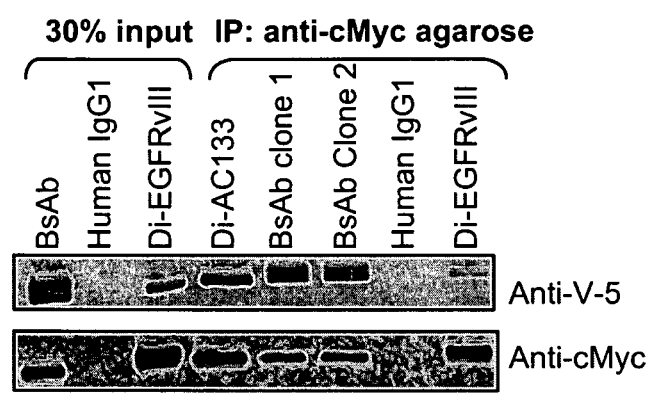

Eukaryotic Expression and Purification of Bispecific and Mono-Specific Minibodies:

Since bacterial expression systems do not carry out the same post-translational modifications as in the eukaryotic system, we subcloned the scFv of EGFRvIII and AC133 into the pBudCE4.1 bicistronic expression vector (FIG. 4A). We expressed the minibody in HEK293 cells which secretes the protein into the media and used metal affinity columns to purify the protein. The presence of both chains was verified by western blotting for either c-myc or V-5 (FIG. 4B). We confirmed that these chains dimerized by immunoprecipitating 1 µg of purified minibody with anti-cmyc-agarose and then western blotting with Anti-V5 (FIG. 4C) which confirmed the presence of both the chains in the dimer. Using a non-reducing gel we confirmed that a majority of the BsAb was being folded as a dimer based on its migration at the expected molecular weight of 150 KD (FIG. 4B middle panel). From here on we refer to the scFv:EGFRvIII/scFv: AC133 bispecific antibody as BsAb, the Di-scFv-EGFRvIII minibody as Di-EGFRvIII and the Di-scFv-AC133 as Di-AC133 minibody.

Affinity Analysis of the BsA:

We first explored if the BsAb showed differential binding to cells expressing both antigens. We co-transfected NIH3T3 cells with cDNA of increasing amounts of CD133 and decreasing amounts of EGFRvIII. Plasma membrane fractions were isolated after 48 hrs and adsorbed onto 96 well ELISA plates and incubated with the different minibodies. The BsAb had the highest binding for the membrane fraction from cells expressing both epitopes, where as the Di-EGFRvIII and Di-AC133 had the highest affinity for membrane fraction of cells expressing the highest levels of EGFRvIII or CD133 respectively (FIG. 5A). To assess the relative binding affinity of the different minibody constructs, we carried out a series of titration experiments where the affinity of the BsAb was compared to that of the individual Di-scFv's using the membrane fraction of NIH3T3 cells that had been transfected with either a 1:1 (FIG. 5B), 5:1 (FIG. 5C) or 1:5 (FIG. 5D) ratio of EGFRvIII:CD133. These experiments showed that the BsAb has the highest affinity when both epitopes are accessible.

Figure 6A:
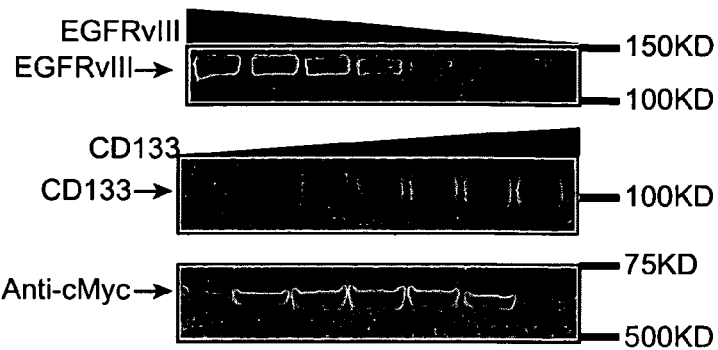
FIG. 6: To analyze the affinity of the BsAb to epitopes expressed in live cells we utilized a live cell pull down assay where BsAb bound to cells was analyzed by western blot or ELISA. Using U87MG cells we observed that maximum binding of minibody occurred with cells expressing both epitopes even when the expression of individual epitopes was higher in single epitope expressing cells (A). Further it was observed that accessibility of epitopes was not sufficient for BsAb binding since independent expression of the EGFRvIII and CD133 in individual cells but in the same mixture was not able to pull down the BsAb as efficiently as the co-expression of CD133 and EGFRvIII in the same cell (B). This is further demonstrated in a more quantitative manner where the surface bound minibodies are stripped using a pH2.5 glycine buffer and quantitated using a direct ELISA assay (C). We titrated the minibodies over cells expressing different epitopes and analyzed them for minibody retention. BsAb was seen to have a significantly higher binding to cells expressing both epitopes.

The above experiments were carried out under detergent extraction conditions where the epitopes may not be in their native conditions which could affect relative affinities. To exclude that this is a problem, we transfected NIH3T3 cells with decreasing amounts of EGFRvIII and increasing amounts of CD133. 48 hrs after transfection, the cells were dissociated and live cell immunoprecipitation was carried out using the three minibodies. The cell-minibody complex was lysed and the levels of the transfected molecule or minibody were analyzed by western blot. We observed that the maximum pull down of cells occurred at a stochiometric transfection ratio of 1:1 (CD133:EGFRvIII) suggesting that the BsAb preferentially recognized cells expressing both antigens (FIG. 6A). We confirmed these results by performing the tranfections in a human glioma line, U87.

Figure 6B:
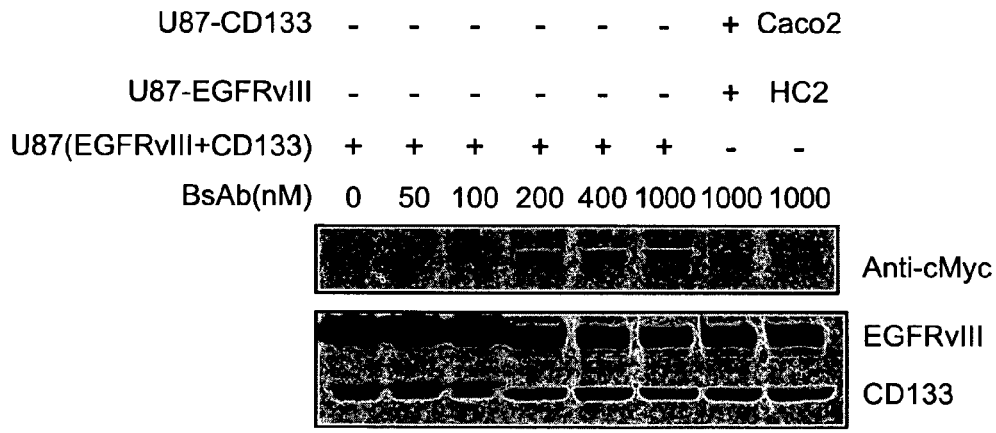

To confirm these results on a glioblastoma cell line and to verify that glioblastoma cells expressing both antigens were being recognized by the BsAb, we used the U87MG glioma cell line. Non-enzymatically dissociated U87MG cells expressing equivalent amounts of EGFRvIII and CD133 were incubated with increasing amount of BsAb (0 nm to 1000 nm). In addition, we mixed equal numbers of U87 cells expressing either EGFRvIII or CD133 and then incubated cells with the BsAb. As an additional control, we also mixed equal numbers of Caco-2 cells (express CD133) and HC2 cells (express EGFRvIII (Moscatello et al. (1996) Oncogene 13, 85-96)) and incubated these with BsAb. We carried out a live cell pull down with the minibodies and analyzed the levels of the bound antibody by western blot (FIG. 6B). We saw that the dual expressing cells bound BsAb at concentration as low as 200 nm, whereas the mixtures of cells expressing each antigen separately showed very little pull down of the BsAb at 1000 nm. These results suggest that the minibody preferentially binds to cells expressing both epitopes.

Figure 6C:
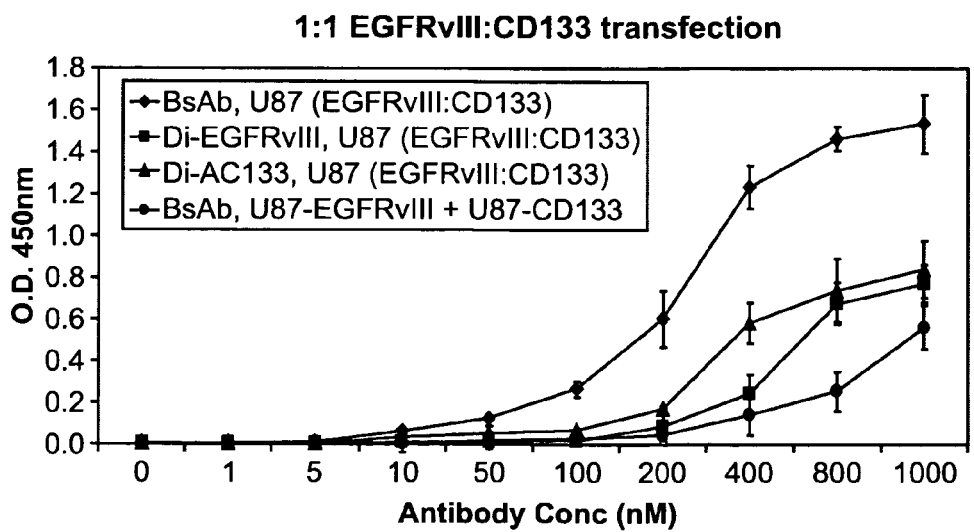
Figure 7:
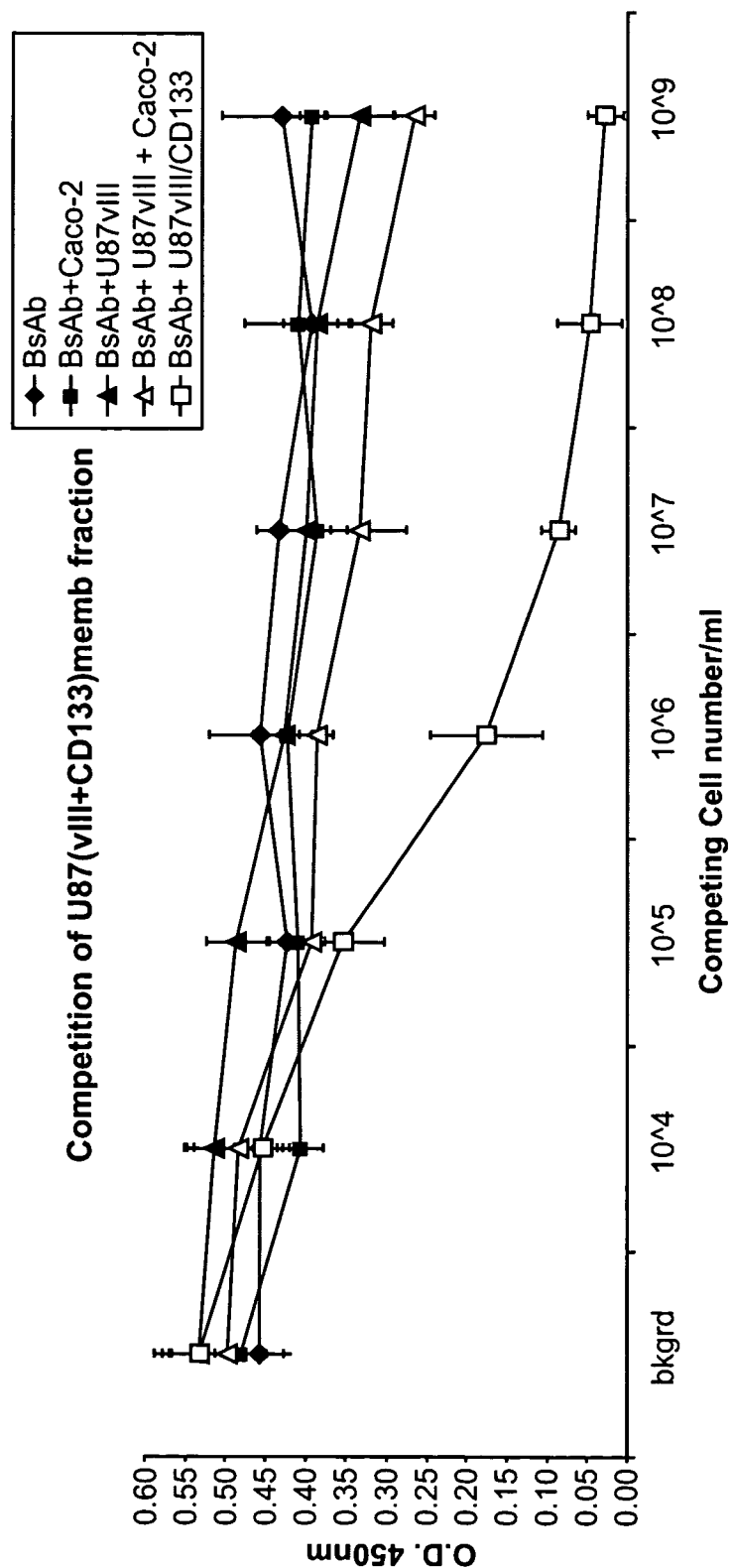
FIG. 7: Competitive binding of BsAb to EGFRvIII$^+$CD133$^+$ cells. Using membrane fraction of cells ($10^5$ cells/well) as bait, BsAb pre-incubated with cells lines expressing different epitopes, it is seen that the membrane fraction is able to competitively bind to the BsAb even in the presence of $10^9$ cells. Only when EGFRvIII$^+$CD133$^+$ are used is the BsAb not retained on the plate. This strongly suggests that the BsAb preferentially and competitively binds to cells expressing both epitopes.

To verify that the antibody that we are detecting lies on the cell surface and does not represent antibody that has been non-specifically internalized, we carried out a similar protocol but with the modification that instead of lysing the cell-minibody complex we stripped the cells with pH 2.5 glycine buffer to remove only surface bound antibody. We carried out a direct ELISA to assay the levels of surface stripped BsAb. This assay showed that the BsAb was specifically bound to cells expressing both antigens at concentrations as low as 50 nM with almost 6 fold higher binding at 200 nM in comparison to cells that did not express these proteins (FIG. 6C). In comparison to either Di-AC133 or Di-EGFRvIII, we again observed that the BsAb also showed significantly higher binding at the 50 nm concentration and nearly 6 fold higher binding at 200 nm. These results confirm that the BsAb is binding to the cell surface in a highly specific fashion.

BsAb Competitively Binds to Cells Expressing Both Epitopes.

To target brain tumor initiating cells, it is desirable that the reagent used should be able to distinguish between the stem cell population and the differentiated population. This is especially true since the stem cell population may constitute as low as 0.01% to 3% of the total tumor population (Singh et al. (2004) *Nature* 432, 396-401). To test whether the BsAb can indeed distinguish between a small percentage of cells expressing CD133/EGFRvIII vs. cells expressing either EGFRvIII or CD133 alone, we utilized a competitive sandwich ELISA assay. The membrane fraction from $1 \times 10^5$ U87: EGFRvIII/CD133 cells per well was coated onto a 96 well plate. We incubated BsAb (400 nm) with U87 cells lines expressing either or both epitopes at cell-concentrations ranging from $10^4$ cells/100 µl to $10^9$ cells/100 µl. The cells and antibody mix was added to the coated membrane fraction without washing and incubated for 15 mins at 4° C. Cells were then washed off and membrane fraction bound BsAb was quantitated using an anti-myc-HRP Ab. We observed that U87 cells expressing both antigens were most successful in retaining BsAb as compared to cells expressing EGFRvIII or CD133 alone. In other words the membrane fraction, which expressed both epitopes, was able to compete the BsAb from cells expressing only one of the epitopes even when the cells expressing both epitopes were mixed together.

BsAb Binds Efficiently to Primary GBM Derived Neurospheres:

Having confirmed that the BsAb had ideal properties for the specific recognition of cells that expressed both CD133 and EGFRvIII, we sought to demonstrate this reagent could specifically target glioblastoma CSC expressing both proteins. When neural stem cells are grown in a defined media containing factors which promote self renewal and prevent differentiation (Reynolds et al (1992) *Science* (New York, N.Y. 255, 1707-1710), they give rise to spheres that contain a high fraction of stem cells When these spheres are injected into the brains of mice they give rise to all neural lineages. Similarly, when GBMs cells are propagated in nearly identical media, they form spheres that when injected into mice will readily form tumors (Singh et al. (2003) *Cancer research* 63, 5821-5828; Uchida et al. (2000) *Proceedings of the National Academy of Sciences of the United States of America* 97, 14720-14725). Genetic analysis and microarray expression profiling has confirmed that these spheres faithfully recapitulate the original tumor (Lee et al. (2006) *Cancer cell* 9, 391-403) including the presence of EGF receptor amplification. Thus, these tumor spheres contain a high fraction of CSCs and have been used as a cell line model for the progagation of CSCs.

Figure 8A:
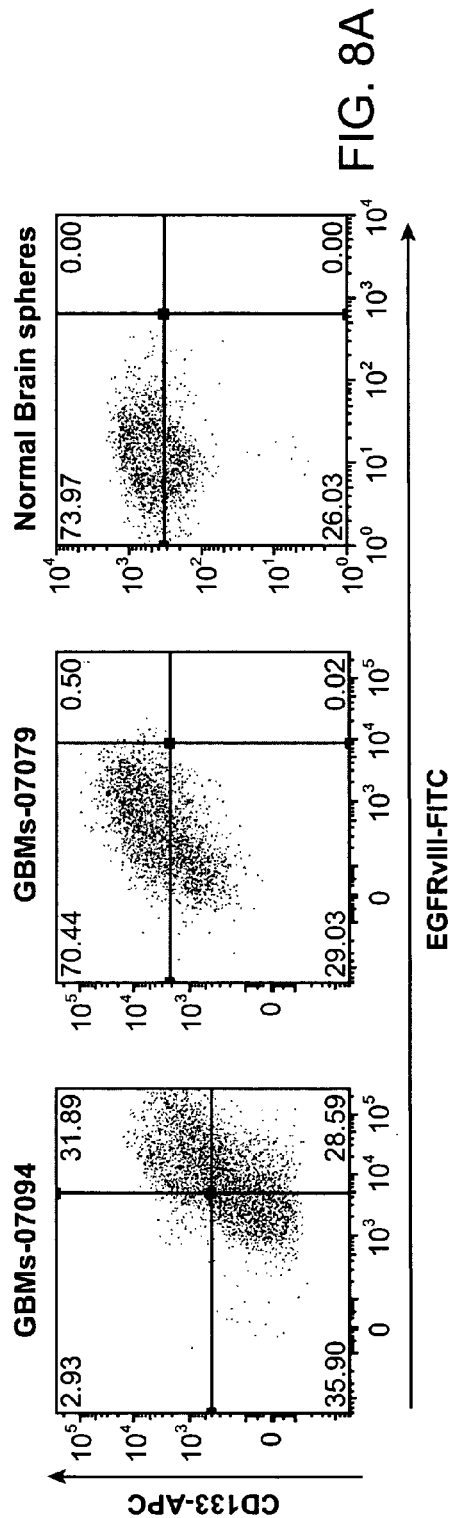
FIG. 8: BsAb binds preferentially to EGFRvIII$^+$CD133$^+$ primary human tumor cells. (A) Using flow cytometry of dissociated neurospheres we evaluated the expression levels of CD133 and EGFRvIII in GBM or Normal derived neurospheres. Shown here is representative plots of three such neurosphere lines which were EGFRvIII$^+$CD133$^+$ (GBMs-07064: Left), EGFRvIII$^-$CD133$^+$ (GBMs-07079: middle) or EGFRvIII$^-$CD133$^+$ (Normal Brain: right). (B) These neurospheres were used for live cell immunoprecipitation of BsAb and surface bound BsAb was quantitated by ELISA. The assay shows the inability of BsAb to bind to EGFRvIII$^-$CD133$^+$ cells or normal neural stem cells.
Figure 8B:
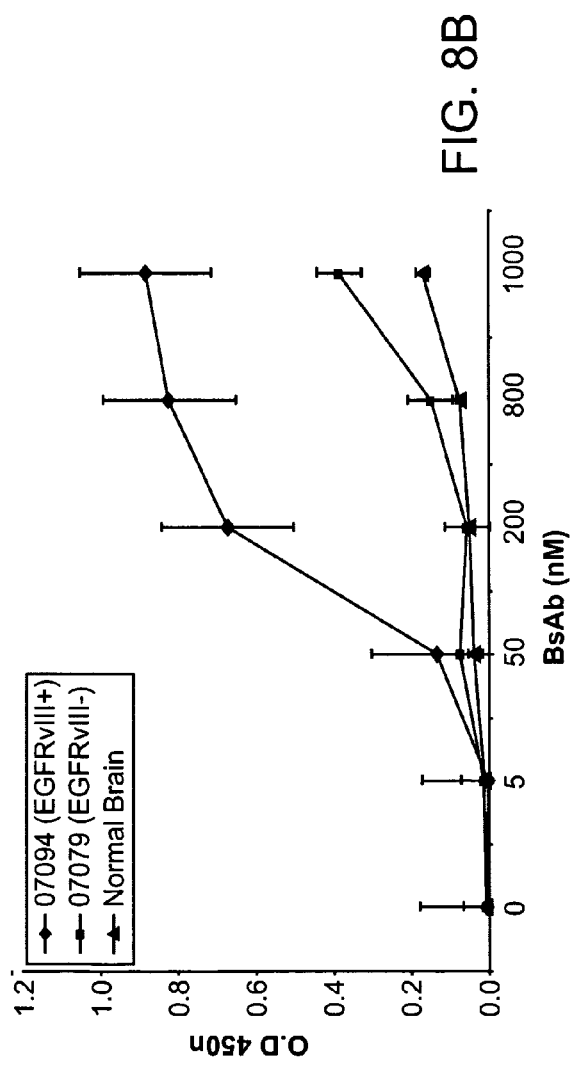

We tested whether the BsAb was selective for primary GBM derived neurospheres which expressed EGFRvIII and CD133. We have isolated several neurosphere lines that we have tested for expression of EGFRvIII and CD133. The 07094 spheres express both EGFRvIII and CD133 while the 07079 line only expresses CD133. As an additional control we used neurospheres derived from the normal brain of an epileptic patient. All neurospheres had been maintained in culture for 30 to 60 days and had undergone less than 3 passages. We dissociated these neurospheres and carried out a live cell immunoprecipitation similar to that described in FIG. 8. The surface bound BsAb was stripped and quantitated using ELISA. Here we observed that the BsAb bound to tumor spheres from GBM 07094 extremely efficiently with a 2 fold difference in binding observed at concentrations as low as 50 nM and a 6 fold difference using 200 nM antibody as compared to spheres from either GBM 07079 or normal brain. These results suggest that the BsAb will target CSC expressing EGFRvIII in a specific fashion but not normal neural stem cells or tumor cells expressing only CD133.

The BsAb Induces Specific Cell Killing of Glioblastoma Cells Expressing EGFRvIII and CD133.

Figure 9B:
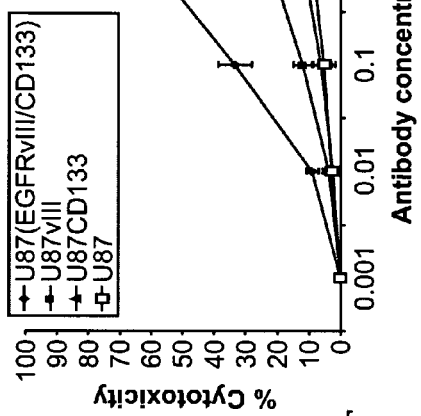
FIG. 9: Cytotoxicity induced by BsAb is targeted towards EGFRvIII$^+$CD133$^+$ cells. (A) using a coupled luminescence assay we observed the ability of BsAb to induce a 12-fold higher cytotoxicity at E:T ratio of 5:1 for EGFRvIII$^+$CD133$^+$ cells compared to the EGFRvIII$^+$ EGFRvIII$^+$ or CD133$^+$ cells. (B) further the BsAb was able to kill cells at concentrations as low as 0.1 ug/ml. (C) Using an E:T ratio of 10:1 and antibody concentration of 1 ug/ml we analyzed the efficiency of the BsAb to induce cytotoxicity. BsAb had the highest cytotoxicity as compared to the monospecific antibodies. (D) Shows the ability of the BsAb to specifically and efficiently target either dissociated neurospheres (07094, 07079, normal brain-1 & normal brain-2) or freshly resected human GBM tissue (08016, 62408, 71408) dependent upon their expression of EGFRvIII and CD133. Dissociated which were EGFRvIII$^+$CD133$^+$ had high cell lysis where as cells expressing only one of the epitopes had poor lysis. Significantly, normal neural stem cells from epileptic patients showed the lowest lysis.
Figure 9A:
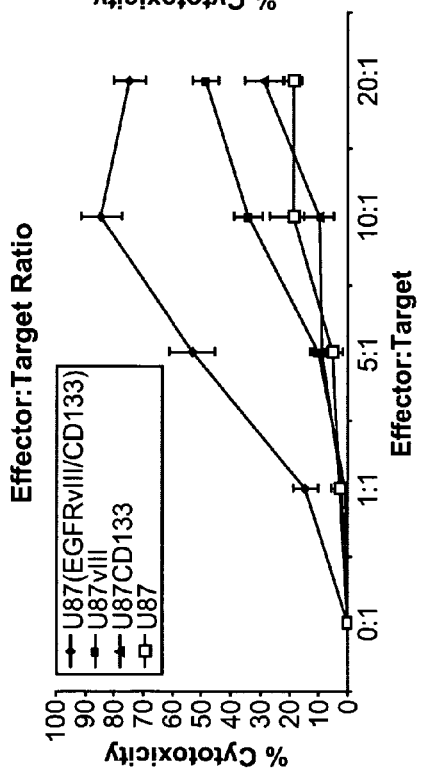
Figure 9D:
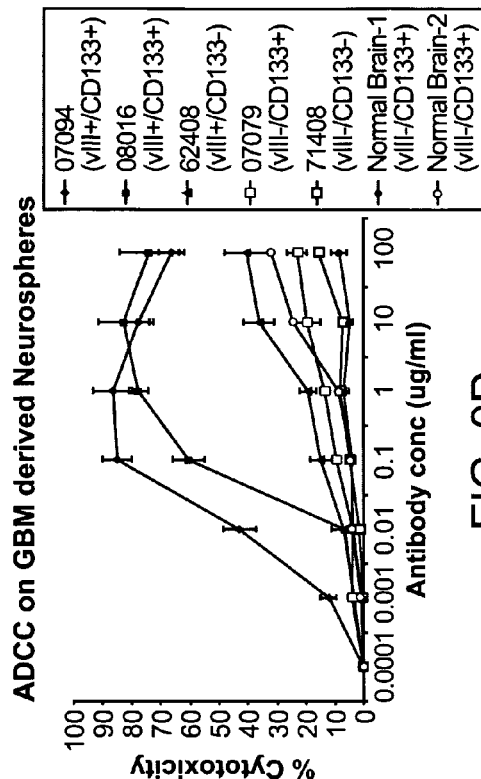
Figure 9C:
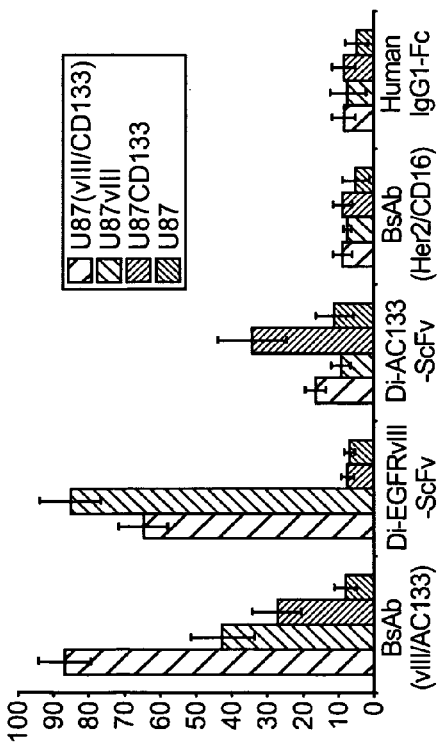

Finally, we sought to demonstrate that the BsAb could lead to effective cell killing of cells expressing both antigens. We used a coupled luminescence method (Ogbomo et al. (2006) *Biochemical and biophysical research communications* 339, 375-37) to determine whether the bispecific minibody format could induce the cytotoxicity of cells that co-express EGFRvIII/CD133 using human CD16-expressing NK cells as the effectors. Donor buffy coats were used to isolate CD16+ cells as described in methods. The first experiments used as targets U87 cells expressing CD133/EGFRvIII, CD133 alone, EGFRvIII alone, or native U87 cells. Effector to target ratios of 0:1, 1:1, 5:1, 10:1, 20:1 were tested. Samples were plated in triplicate, and one control set of wells contained both effector and target cells but no antibody to control for spontaneous lysis. An antibody concentration of 400 nm was used to achieve binding to all cell types because this showed high differential binding of the BsAb to EGFRvIII/CD133 expressing cells. The BsAb was able to induce ADCC on U87-EGFRvIII/CD133 expressing cells at a ratio of 5:1 whereas a higher E:T ratio was required for cells expressing only a single epitope (FIG. 9A). We then explored the concentration range in which the BsAb was effective at ADCC. Using a constant E:T ratio of 10:1 we found that as little as 1 µg/ml (8.3 nM) of BsAb was sufficient to induce cytotoxicity of more than 60% of the U87 cells expressing EGFRvIII/CD133, which has 3 fold greater lysis than seen in U87 cells expressing EGFRvIII and 12 fold greater than in cells CD133 alone (FIG. 9B). We further tested the efficiency of the BsAb to induce ADCC as compared to di-EGFRvIII-scFv, di-CD133-scFv and as a further control, the anti-HER2/neu-anti-CD16 bispecific minibody (Shahied et al. (2004) *The Journal of biological chemistry* 279, 53907-53914). Using an effector:target ratio of 10:1 and a concentration of 1 µg/ml of each minibody, we found that the BsAb was able to induce cytotoxicity in 86% of U87-EGFRvIII/CD133 cells and 42.5% in U87vIII but only 27.3% in U87-CD133 cells. Similarly we saw that Di-EGFRvIII-scFv was efficient in inducing cytotoxicity in U87-EGFRvIII/CD133 and U87vIII cells but not in U87-CD133 cells. The Di-CD133-scFv was the least effective at inducing ADCC among the recombinant antibodies. As negative controls, we used a previously defined anti-HER2/neu-anti-CD16 Bispecific minibody (Lorimer et al. (1996) *Proceedings of the National Academy of Sciences of the United States of America* 93, 14815-14820) and human IgG1. None of these antibodies were able to induce significant ADCC in the target cells lines. These results demonstrate that the BsAb can efficiently kill cells expressing EGFRvIII/CD133 at very low antibody concentrations.

The Anti-EGFRvIII:Anti-CD133 Bispecific Minibody Efficiently and Differentially Targets Dissociated GBM Cells:

The previous experiments used cells expressing defined amounts of EGFRvIII and CD133. We wished to demonstrate that the BsAb could effectively lyse tumor cells from human patients. We used freshly dissociated brain tumor cells and dissociated neurospheres derived from primary human GBM. In addition we used dissociated cells from neurospheres derived from epileptic brain resections as negative controls. These dissociated cells were FACS analyzed for EGFRvIII and CD133 expression status. We found that the BsAb caused maximum lysis in cells expressing both EGFRvIII and CD133 and moderate lysis of the cell line expressing EGFRvIII alone (62408), but there was far less lysis of cells that expressed CD133 alone (07079 and normal brain #1 and #2). It also showed significant lysis of cells expressing only EGFRvIII and not CD133 but it showed minimum lysis of cells expressing only CD133 (i.e GBM07079, normal brain). Collectively, this data demonstrates that the BsAb is highly effective in targeting primary tumor cells expressing EGFRvIII and CD133 and is not effective at lysing normal brain stem cells.

Experimental Procedures:

Cloning of Single Chain Variable Fragment:

The anti-CD133 scFv was obtained by PCR amplification of the variable regions of the light (VL) and heavy (VH) chains from AC133.1 hybridoma cells obtained from ATCC (ATCC No. HB-12346, Yin et al. (1997) *Blood* 90, 5002-5012). RNA was extracted from HB12346 cells and primers were used to amplify the VL and VH regions. The PCR fragments for the Vl and Vh regions were fused together using Splicing by Overlapping Extension PCR (SOE-PCR) to create the AC133 scFv. This was then subcloned into either the pET32 (Novagen/EMD Gibbstown, N.J.) bacterial expression vector or pBudCE4 (Bicistronic eukaryotic expression vector; Invitrogen, Carlsbad, Calif.). Anti-EGFRvIII scFv was artificially synthesized based on the published sequence available from Genbank (accession no. U76382, Okamoto et al. (2003) *Cancer science* 94, 50-56).

Expression and Purification of Minibody Constructs—

The pBudCE4:Her2/neu:CD16 bispecific minibody was obtained as a kind gift from Dr Louis Weiner. This construct has scFv against Her2/neu and CD16 in a bi-cistronic vector and CH3 gene with "knobs-into-holes" configuration. Thus, this single construct leads to the production of a dimeric antibody or di-body. Additional sequences corresponding to a V5 and His6 tag are present in at the 3'-end of the anti-EGFRvIII binding arm, whereas the anti-CD133 binding arm contains a Myc epitope as well as a His6 tag at its 3'-end. We replaced the scFv's for Her2/neu with scFv of anti-EGFRvIII Ab (MR1-1) and anti-CD16 scFv with the gene for scFv of anti-CD133 (Clone AC133). As controls, minibodies containing either two scFv chains against AC133 or EGFRvIII were also created.

The pBudCE4-bispecific and monospecific minibody vectors were stably transfected into HEK 293 cells. Zeocin was used for the selection of positive HEK 293 cell clones. Cells supernatants were collected, centrifuged, and filtered prior to loading onto a 5-ml His-Trap column (Amersham Biosciences). Nonspecific proteins were removed from the column by first washing with phosphate buffer containing 10 mM imidazole followed by a second phosphate buffer wash containing 50 mM imidazole. Minibody proteins were then batch eluted using a 500 mM imidazole phosphate buffer. Fractions containing the proteins were combined and dialyzed into PBS. After visualization on an SDS-PAGE gel, fractions containing the dimeric minibody were combined. Concentration measurement was determined by a Bio-Rad protein assay (Bio-Rad Laboratories).

Cell Lines, Reagents and Antibodies Utilized:

Parental NIH3T3, A431 and U87MG gliomas cells were obtained from ATCC. U87 cells expressing EGFRvIII (U87vIII) was a kind gift of Dr Donald O'Rourke. NIH 3T3 cells stably expressing NIH3T3-HC2 and NIH3T3-CO12 have been previously described (Moscatello et al. (1996) *Oncogene* 13, 85-96). U87-EGFRvIII/CD133 double expressing cells lines were generated by stable transfection of EGFRvIII and CD133. The CD133 clone was obtained from Plasmid Information Database (PlasmID) maintained by Dana-Farber/Harvard Cancer Center DNA Resource Core. The CD133 gene was PCR amplified from the pDONR22.1 plasmid, and BamHI and XhoI restriction sites added to the 5' and 3' end. This was further subcloned into pCR3.1 vector. EGFRvIII was also subcloned into the pCR3.1 vector from LTR-HC2 expression vector.

Dissociation of primary human brain tumors and culture:

Freshly resected human brain tumor samples were obtained from the Stanford University brain bank and Stanford University tissue under IRB approved protocols. Tissue samples were minced using a No. 10 scalpel and dissociated using a collagenase (1 mg/ml) based dissociation media at 37 C. with frequent agitation. Dissociated cells were treated with ACK/RBC lysis buffer (0.15M NH4Cl, 1.0 mM KHCO3 and). 1 mM $Na_2$-EDTA and plated for either neurosphere formation or FACS analysis.

Flow Cytometry:

Freshly dissociated cells were stained with a monoclonal antibody anti-EGFRvIII (G100) or with CD133/1 and CD133/2 (Miltenyi) and analyzed on a LSR FACS machine (BD biosciences) at the Stanford University FACS facility. Cells from the primary tumor itself were used for compensation using an anti-MHC I biotin antibody. Secondary antibodies used were streptavidin-FITC or streptavidin-APC. Appropriate isotype controls were used to control for non-specific isotype background.

Immunoprecipitation and Western Blot Analysis:

Purified bispecific or monospecific minibody proteins were diluted in PBS and incubated with agarose conjugated anti-myc antibody (Sigma). After washing three timesin PBST (PBS+0.5% Tween 20), the minibody was eluted from agarose using SDS-PAGE solublization buffer and separated on an SDS-PAGE gel. Minibodies were transferred onto nitrocellulose and immunoblotted using anti-V5 antibody.

Live Cell Immunoprecipitation.

Cell lines expressing EGFRvIII, CD133 or both were non-enzymatically dissociated using cell dissociation buffer (Invitrogen). After washing three times with HBSS (with Ca/Mg), cells were blocked with human γ-globin (Jackson Immuno research) for 10 minutes on ice. Cells were counted and a fixed number of viable cells were incubated with various concentrations of minibodies for 10 minutes at 4° C. Cells were then spun down at 300 g for 10 minutes and washed thrice with HBSS with 1% BSA. For a qualitative analysis of affinity, the cells were lysed with SDS-PAGE buffer and processed for western-blot analysis. Membranes were probed with either anti-CD133 (clone W6B3C1, Miltenyi Biotech), anti-EGFRvIII or anti-V5 antibody. For quantitative analysis of surface bound minibody, live cells were resuspended in 300 ul 500 mM glycine stripping buffer (pH2.2) for 2 min at 40 C., spun at 300 g and supernatant collected (200 ul). Eluted minibody was neutralized in 600 ul 1M Tris (pH8.0). Neutralized Minibodies were then adsorbed on 96 well plates and detected using HRP labeled anti-myc antibody (Genscript).

Plasma Membrane Preparation and ELISA:

Cells were dissociated using cell dissociation buffer (Invitrogen) and with cold PBS three times and resuspended in 25 mM Tris (pH7.4) and 320 mM Sucrose. Cells were then lysed using low strength sonication with an output of 4.5 W for 10 seconds three times. Lysed samples were then centrifuged at 100,000 g for 1 hour. The supernatant was discarded and pellet resuspended in 50 mM Tris (pH 7.4). The pellet was once again centrifuged at 100,000 g for 1 h and the pellet resuspended in 0.02 M bicarbonate buffer (pH9.6). Protein quantitation was carried out and known concentration of protein was adsorbed on a 96 well ELISA plate (BD Falcon).

ELISA Screening for Minibody Affinity:

Plasma membrane fraction of cells expressing different levels of epitopes were adsorbed on a 96 well plate overnight at 4 C. Cells were blocked with human γ-globulin (Jackson Immunoresearch) and subsequently incubated with different concentration of minibodies. The secondary antibody used to detect bound minibody was THE™ Anti-c-Myc-tag [HRP] mAb (Genscript). Plates were developed using the SureBlue TMB Microwell Substrate (KPL). For the ELISA to measure antibody bound to cells in the previously described live cell immunoprecipitation, supernatant from the cells was neutralized and coated onto 96 well plate and detected using THE™Anti-c-Myc-tag [HRP] mAb (Genscript) and SureBlue TMB Microwell Substrate (KPL).

NK Cell Purification and Culture:

Peripheral blood mononuclear cells (PBMCs) from healthy volunteer blood donations at the Stanford Blood Center were isolated by Ficoll density gradient centrifugation. NK cells were purified using anti-CD56-coated microbeads (Miltenyi Biotec, Auburn, Calif.), followed by 2 rounds of positive selection using autoMACS (Miltenyi Biotec) and CD3-positive cells were subsequently depleted using anti-CD3 coated magnetic beads (Dynabeads, Invitrogen, Carlsbad, Calif.). The cells were cultured in Iscove's modified Dulbecco medium (Invitrogen) supplemented with 10% fetal calf serum, 2% human serum, 2 mM L-glutamine, 100 U/mL penicillin, 100 µg/mL streptomycin, and 10 ng/mL IL-15 (Peprotech, Rocky Hill, N.J.).

Cytotoxicity Assay:

The minibodies were tested for their ability to induce antibodydependent cellular cytotoxicity (ADCC). NK cells were tested for cytolytic activity against target cells expressing the various epitopes, using the "aCella-Tox" kit (Cell Technology, Mountain View, Calif.). This kit employs a coupled luminescent technology for the detection of cytotoxicity. Viable target cells were plated in triplicate (5000 cells/well) in a 96-well white plate (Greiner Bio-One, Frickenhausen, Germany). Minibodies were added at the indicated concentration followed by the effector cells (NK cells) at indicated E:T ratios. Total spontaneous cell death was calculated for each E:T ratio with and without the presence of minibody as used as a background count. A modified RIPA buffer (0.9% NP-40+0.1% SDS) was used to assay for maximum release. The protocol was carried out according to the manufacturers' recommendation and luciferase activity was measured using LB96V MicroLumat Plus luminometer (Berthold). The percent cytotoxicity was calculated by [(experimental G3PDH release-spontaneous G3PDH release from effector cells alone-spontaneous G3PDH release from target cells alone)/ (maximum G3PDH release from target cells-spontaneous G3PDH release from target cells)]·100.

TABLE 1

EGFRvIII and CD133 Co-expression in freshly resected human GBM samples.

| Tumor | % Cells Expressing EGFRvIII | % Cells Expressing CD133 | Expected incidence if Co-expression is random | Actual % Cells vIII+/CD133+ | Fold Enrichment over random expression | % CD133+ expressing EGFRvIII | % EGFRvIII+ Expressing CD133 |
|---|---|---|---|---|---|---|---|
| GBM1 | 9.48 | 17.75 | 0.73 | 2.10 | 7 | 11.83 | 22.22 |
| GBM2 | 11.57 | 9.06 | 1.24 | 4.628 | 5 | 51.06 | 40.00 |
| GBM3 | 3.05 | 6.22 | 0.31 | 1.7 | 16 | 27.97 | 57.1 |
| GBM4 | 0.5 | 0.072 | 0.02 | 0.042 | 63 | 58.33 | 8.47 |
| GBM5 | 7.05 | 7.75 | 0.48 | 0.705 | 11 | 9.09 | 10.00 |
| GBM6 | 10.15 | 9.15 | 0.93 | 8.01 | 9 | 87.97 | 78.91 |
| GBM7 | 8.25 | 6.80 | 0.56 | 5.37 | 10 | 78.91 | 65.13 |
| GBM8 | 12.40 | 10.82 | 1.34 | 10.06 | 7 | 92.91 | 81.13 |
| GBM9 | 8.54 | 9.14 | 0.78 | 2.37 | 3 | 25.92 | 38.41 |
| GBM10 | 18.97 | 18.64 | 3.54 | 10.10 | 3 | 54.18 | 53.24 |
| GBM11 | 12.99 | 8.93 | 1.16 | 5.59 | 5 | 62.59 | 43.03 |
| GBM12 | 23.58 | 2.87 | 0.67 | 1.99 | 3 | 69.33 | 8.43 |

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. Moreover, due to biological functional equivalency considerations, changes can be made in protein structure without affecting the biological action in kind or amount. All such modifications are intended to be included within the scope of the appended claims.

What is claimed is:

1. A method for treating glioma, medulloblastoma or glioblastoma comprising administering to a subject in need thereof a scFv:EGFRviii/scFv:AC133 bispecific minibody, wherein said subject has $CD133^+/EGFRviii^+$ glioma, $CD133^+/EGFRviii^+$ medulloblastoma or $CD133^+/EGFRviii^+$ glioblastoma.

* * * * *